US011384160B1

(12) United States Patent
Charara et al.

(10) Patent No.: US 11,384,160 B1
(45) Date of Patent: Jul. 12, 2022

(54) METHOD OF MAKING A BETA GLUCAN COMPOUND

(71) Applicant: TISSUE REPAIR LTD, Sydney (AU)

(72) Inventors: Anthony Charara, Sydney (AU); Mark Deacon Shaw, Sydney (AU)

(73) Assignee: TISSUE REPAIR LTD, Sydney (AU)

( * ) Notice: Subject to any disclaimer, the term of this patent is extended or adjusted under 35 U.S.C. 154(b) by 0 days.

(21) Appl. No.: 17/390,809

(22) Filed: Jul. 30, 2021

(51) Int. Cl.
| | |
|---|---|
| A61K 8/73 | (2006.01) |
| C08B 37/00 | (2006.01) |
| A61K 9/00 | (2006.01) |
| A61K 31/716 | (2006.01) |
| A61Q 19/08 | (2006.01) |
| A61K 8/04 | (2006.01) |
| A61P 17/02 | (2006.01) |
| A61K 9/06 | (2006.01) |

(52) U.S. Cl.
CPC .......... C08B 37/0024 (2013.01); A61K 8/042 (2013.01); A61K 8/73 (2013.01); A61K 9/0014 (2013.01); A61K 9/06 (2013.01); A61K 31/716 (2013.01); A61P 17/02 (2018.01); A61Q 19/08 (2013.01)

(58) Field of Classification Search
None
See application file for complete search history.

(56) References Cited

U.S. PATENT DOCUMENTS

| | | |
|---|---|---|
| 3,975,553 A | 8/1976 | Griffon |
| 4,138,479 A | 2/1979 | Truscheit et al. |
| 4,810,646 A | 3/1989 | Jamas et al. |
| 4,833,131 A | 5/1989 | Williams et al. |
| 4,992,540 A | 2/1991 | Jamas et al. |
| 5,019,391 A | 5/1991 | Bunte et al. |
| 5,158,772 A | 10/1992 | Davis |
| 5,223,491 A | 6/1993 | Donzis |
| 5,980,918 A | 11/1999 | Klein |
| 6,168,799 B1 | 1/2001 | Klein |
| 6,242,594 B1 * | 6/2001 | Kelly .................. A61K 31/716 536/124 |
| 6,342,486 B1 | 1/2002 | Zulli et al. |
| 6,369,216 B1 | 4/2002 | Patchen et al. |
| 6,476,003 B1 | 11/2002 | Jordan et al. |
| 6,531,132 B1 | 3/2003 | Paufique |
| 6,875,754 B1 | 4/2005 | Griesbach et al. |
| 7,431,940 B2 | 10/2008 | Zulli et al. |
| 7,622,575 B2 | 11/2009 | Kelly |
| 7,648,968 B2 | 1/2010 | Kelly |
| 7,776,843 B2 | 8/2010 | Kelly |
| 9,187,575 B2 | 11/2015 | Sauter et al. |
| 9,314,432 B2 | 4/2016 | Engstad et al. |
| 9,623,043 B2 | 4/2017 | Engstad et al. |
| 9,956,245 B2 | 5/2018 | Engstad et al. |
| 10,117,937 B2 | 11/2018 | Yao et al. |
| 2002/0032170 A1 | 3/2002 | Jamas et al. |
| 2002/0150585 A1 * | 10/2002 | Marciani ............... C08B 37/003 514/54 |
| 2007/0053960 A1 | 3/2007 | Brown et al. |
| 2008/0160043 A1 | 7/2008 | Kim et al. |
| 2011/0028709 A1 | 2/2011 | Deacon-Shaw et al. |
| 2011/0053855 A1 | 3/2011 | Koenig |
| 2011/0065911 A1 | 3/2011 | Koenig |
| 2011/0301118 A1 | 12/2011 | Koenig |
| 2012/0003178 A1 | 1/2012 | Koenic |
| 2019/0343752 A1 | 11/2019 | Johnson et al. |

FOREIGN PATENT DOCUMENTS

| | | |
|---|---|---|
| CN | 110522761 A | 12/2019 |
| CN | 111773239 A | 10/2020 |
| JP | 2019059740 A | 12/2019 |
| KR | 102096545 B1 | 9/2019 |
| WO | 1996028476 A1 | 9/1996 |
| WO | 1999033439 A1 | 7/1999 |
| WO | 2009055848 A1 | 5/2009 |
| WO | 2009103116 A1 | 8/2009 |
| WO | 2010042991 A1 | 4/2010 |
| WO | 2015168741 A1 | 11/2015 |

OTHER PUBLICATIONS

Fang, J. et al. Structure of a Beta Glucan from Gifolia frondosa and its Antitumor Effect by Activating Dectin-1/Syk/NF-kappaB Signaling. Glycoconjuate Journal 29(5-6)365-377, 2012. (Year: 2012).*
Roy, S. et al. Particulate Beta Glucan Induces TNF alpha Production in Wound Macrophages via a Redox Sensitive NF-kappaB Dependent Pathway. Wound Repairand Regeneration 19(3)411-419 May-Jun. 2011. (Year: 2011).*
Mendonca P. et al. Beta Glucan Induces Reactive Oxygen Species in Production in Human Neutrophils to Improve the Killing of Candida albicans . . . PLoS One 9(9)1-13 Sep. 17, 2014. (Year: 2014).*
Murphy E.J. et al, Journal of Fungi "Beta-Glucan Metabolic and Immunomodulatory Properties and Potential for Clinical Application" Dec. 2020 (36 pages).
Medeiros et al, International Journal of Molecular Sciences "Effects of Purified *Saccharomyces cerevisiae* (1-3)-beta-glucan on Venous Ulcer Healing" Jul. 2012 (17 pages).

(Continued)

*Primary Examiner* — Ralph J Gitomer
(74) *Attorney, Agent, or Firm* — Arc IP Law, PC; Joseph J. Mayo

(57) ABSTRACT

Described herein is an isolated biological polysaccharide compound. The biological polysaccharide compound may be characterised by being isolated and having: glycosyl linkages comprising 1:3 linked glucopyranosyl residue of 65-95% wt and 1:6 linked glucopyranosyl residue of 5-25% wt; and a purity of 85-100% β-D-glucan; and a molecular weight of 0.5 to 2.2 MDa; and a TNF-alpha cytokine response in a human bioassay that is at least 1.5 times greater than a negative control TNF-alpha cytokine response in a human bioassay; and being essentially insoluble in aqueous solutions. In a further aspect, methods are described of treating skin by topical application of a vehicle containing the isolated biological polysaccharide to a skin site such as a wound or burn. A method of manufacture is also described.

17 Claims, 18 Drawing Sheets
(11 of 18 Drawing Sheet(s) Filed in Color)

(56) References Cited

OTHER PUBLICATIONS

Lee et al, Biomaterials, "Bio-Artificial Skin Composed of Gelatin and 1-3, 1-6 beta glucan", 2003 (9 pages).
Kiefer, Dale, Life Extension Magazine, "What's Missing from your sunscreen?" Jun. 2007, retrieved from www.lef.org (8 pages).
Delatte et al, Journal of Pediatric Surgery, "Effectiveness of Beta Glucan Collagen for Treatment of Partial-Thickness Burns in Children" 2001 (6 pages).

* cited by examiner

Healed in 12 weeks ulcer size on randomization was 9.4cm2

Presented at Prince Charles hospital wound clinic patient age 84 wound was present for 29 weeks prior to screening

METHOD OF MAKING A BETA GLUCAN COMPOUND

TECHNICAL FIELD

Described herein is an isolated biological polysaccharide compound, methods of use and methods of manufacture thereof. More specifically, the polysaccharide may be a highly pure form of biologically derived polysaccharide and methods of use may be in relation to topical skin treatments. The method of manufacture comprises additional manufacturing steps to art methods that appear to provide an unexpectedly clinically efficacious polysaccharide compound.

BACKGROUND ART

Polysaccharide compounds and related aspects are described herein. For ease of description, the polysaccharides described herein are derived from yeast hence may be interchangeably termed biological polysaccharides, biologically derived polysaccharides, glucans, or β-glucans hereafter.

Biologically derived polysaccharides from yeasts are known compounds made up of glycosyl linkages. Their use for promoting wound repair among other uses is known. Non-cellulosic β-glucans are recognized as potent immunological activators. β-Glucans are generally safe and are known to attenuate the rate of postoperative infection.

Existing art describes in findings about tissue repair, skin care and other uses where one key compound in such products is a yeast cell membrane product. The art describes use of the yeast cell product for treating skin conditions; processes of making β-glucan from yeasts; treatment of skin cell products from yeasts; revitalizing skin using topically applied yeast-derived particulate β-glucan; cereal derived β-glucan for topical treatment of burns as a gel or cream; preparation of small particle glucan using freeze drying; processes of extracting β-glucan using enzymes; using carboxymethyl β-glucan in a carrier to treat skin after laser or chemical peeling treatment; topical application of microparticulate β-glucan for treating skin after laser or chemical peeling treatment; the effects of a purified yeast extract β-glucan with only 1-3 linkages and limited 1-6 side chains; and a gel glucan product derived from *Saccharomyces Cerevisiae*.

Their exists defects in the understanding of the complex relationship between β-glucan structure and their effect profile, together with heterogeneity in the approach to clinical translation, and variations in the approaches to extracting and purifying these agents. These defects have hampered the search for a molecule which has actual demonstrated success in achieving clinically accepted endpoints set by regulators in double bind randomised placebo controlled trials.

To date β-glucans have not succeeded in obtaining drug or biological approval for indications in wound healing. Despite prior art around the molecule for use in wound healing, no β-glucan containing formulation has proven clinical efficacy in double blind placebo controlled human trails in venous leg ulcers or other chronic wounds around regulatory mandated clinical endpoints.

In the inventors experience, the prior art has not solved or described what molecule characterisation produces evidence of clinical efficacy. For example, the art does not describe what the glucan branching structure should be; what the molecular weight should be; what the ideal purity and measured immune response should be and so on; to achieve both regulatory approval around consistency of an end product combined with actual demonstrated clinical efficacy on wound healing endpoints.

No glucan has been approved to date meeting the United States of America Food and Drug Administration (FDA) valid endpoints on clinical trials despite a significant amount of prior art in the field of glucans. The need for valid and efficacious skin treatment remains however and new treatments that are efficacious are of significant value. It is noted that no drug has been approved with therapeutic claims to treat venous leg ulcers in the last 30 years, despite the indication having a massive unmet need.

Specifically, the inventors have identified that the art does not describe:

Accurate characterisation and description of a β-glucan compound which evidences clinical efficacy on gold standard wound healing endpoints set by regulators in treatment of venous leg ulcers and chronic wounds;

Additional processing beyond that described in U.S. Pat. No. 6,242,594 of an insoluble yeast (*Saccharomyces cerevisiae*) derived β-glucan;

A higher purity β-glucan compound than that described in U.S. Pat. No. 6,242,594;

Microparticulate β-glucan;

Unexpected evidenced clinical efficacy in treatment of cosmetic skin conditions and chronic wounds;

Use of topically applied microparticulate biological polysaccharide compound to improve skin quality measured by elastosis and wrinkling.

Use of a biological polysaccharide compound to provide clinical evidence in acceleration in skin quality benefits following laser ablative laser surgery;

Use of a biological polysaccharide compounds to initiate as well as accelerate healing of a venous ulcer;

Proven clinical efficacy in wound healing in human double blind randomised placebo controlled trials;

Proven clinical efficacy in accelerated skin quality as measured by clinical graded improvements elastosis and wrinkling in human double blind randomised placebo controlled trials;

The art also leads away from insoluble biological polysaccharide compounds or insoluble β-glucan itself. The art in fact indicates insoluble β-glucan is highly inflammatory and should not be used in topical wound/skin environments as the excessive inflammatory reaction causes harm and In fact poorer healing outcomes;

Evidence of very high immune response over prior art compounds for wound healing producing an unexpected positive effect;

A biological polysaccharide compound which has achieved positive phase IIB data in the indication of venous leg ulcers as well as cosmesis on endpoints acceptable by the FDA and other regulators to grant a therapeutic label.

Further aspects and advantages of the biological polysaccharide compounds, methods of use and methods of manufacture thereof will become apparent from the ensuing description that is given by way of example only.

SUMMARY

Described herein is, in a highly pure form, an isolated, insoluble biologically derived polysaccharide compound. Methods of use of this compound are described illustrating the higher than expected level of efficacy of the compound, particularly in topical skin treatments. A method of manufacture is also described illustrating alternate/additional manufacturing steps to art methods that appear to provide an unexpectedly efficacious polysaccharide compound.

In a first aspect, there is provided an isolated biological polysaccharide compound characterised by one or more of the following:
  (a) glycosyl linkages comprising 1:3 linked glucopyranosyl residue of 65-95% wt and 1:6 linked glucopyranosyl residue of 5-25% wt;
  (b) a purity of 85-100% β-D-glucan;
  (c) a molecular weight of 0.5 to 2.2 MDa;
  (d) a TNF-alpha cytokine response in a human bioassay that is at least 1.5 times greater than a negative control TNF-alpha cytokine response in a human bioassay;
  (e) being essentially insoluble in aqueous solutions.

In a second aspect, there is provided a method of treating the skin of a patient in need thereof by topical application of a vehicle to a wound site, the vehicle comprising a therapeutically effective amount of an isolated biological polysaccharide compound as claimed in any one of the above claims.

In a third aspect, there is provided the use, in the manufacture of a medicament, of an isolated biological polysaccharide compound substantially as described herein, for topical treatment of the skin of a patient in need thereof.

In a fourth aspect, there is provided a method of manufacturing an isolated biological polysaccharide compound substantially as described above by the steps of:
  selecting yeast cells;
  lysing the cells and collecting the cell wall fragments;
  acidifying then heating the cell wall fragments to remove mannan and chitin
  conducting phase separation with an organic solvent to remove additional mannan and chitin along with proteins, glycogen and lipids;
  separating solvent and other non-polysaccharide compounds via boiling and drying;
the method comprising at least one additional water rinse step after lysing and before acidifying.

The above described isolated biological polysaccharide compound, methods of use and method of manufacture may, comprise a number of advantages, one being that the compound provides an unexpected and optimal immunogenic response for topical treatments without any deleterious inflammatory affects.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Further aspects of the biological polysaccharide compound, methods of use and methods of manufacture thereof will become apparent from the following description that is given by way of example only and with reference to the accompanying drawings in which.

DETAILED DESCRIPTION

Figure 1A:
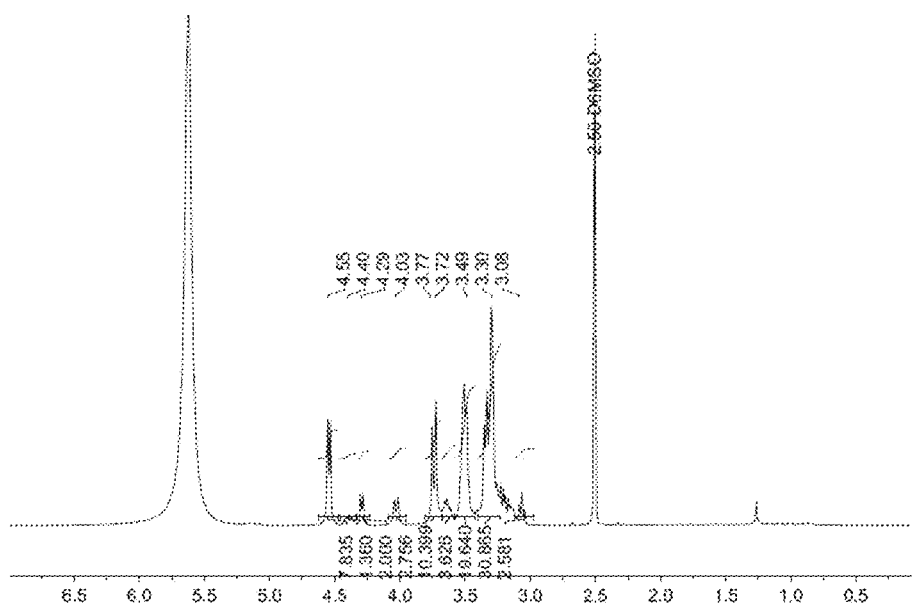
FIGS. 1A and 1B illustrate a 1H NMR graph and the molecule schematically where the described biological polysaccharide is a β-glucan based polysaccharide, with a general structure of (1→3)(1→6)-β-glucan. For simplicity, the primary residues are labelled 'BC', 'Br' and 'SC'. While BC represent the backbone residues, Br represent the branching residues and SC represent the side-chain residues.

As noted above, described herein is, in a highly pure form, an isolated biologically derived polysaccharide compound. Methods of use of this compound are described illustrating the unexpected efficacy of the compound, particularly in topical skin treatments. A method of manufacture is also described illustrating alternate/additional manufacturing steps to art methods that appear to provide an unexpectedly efficacious polysaccharide compound.

For the purposes of this specification, the term 'about' or 'approximately' and grammatical variations thereof mean a quantity, level, degree, value, number, frequency, percentage, dimension, size, amount, weight or length that varies by as much as 30, 25, 20, 15, 10, 9, 8, 7, 6, 5, 4, 3, 2, or 1% to a reference quantity, level, degree, value, number, frequency, percentage, dimension, size, amount, weight or length.

The term 'substantially' or grammatical variations thereof refers to at least about 50%, for example 75%, 85%, 95% or 98%.

The term 'comprise' and grammatical variations thereof shall have an inclusive meaning—i.e. that it will be taken to mean an inclusion of not only the listed components it directly references, but also other non-specified components or elements.

The term 'polysaccharide compound' and grammatical variations thereof as used herein encompass compounds derived from yeast comprising glycosyl linkages. The term 'polysaccharide compound' may be used interchangeably with the terms 'biological polysaccharides', 'biologically derived polysaccharides', 'glucans' or 'β-glucans' hereafter. Reference to one term should not be seen as limiting to use of the other terms unless otherwise specified.

An Isolated Biological Polysaccharide Compound

In a first aspect, there is provided an isolated biological polysaccharide compound characterised by one or more of the following:
(a) glycosyl linkages comprising 1:3 linked glucopyranosyl residue of 65-95% wt and 1:6 linked glucopyranosyl residue of 5-25% wt;
(b) a purity of 85-100% β-D-glucan;
(c) a molecular weight of 0.5 to 2.2 MDa;
(d) a TNF-alpha cytokine response in a human bioassay that is at least 1.5 times greater than a negative control TNF-alpha cytokine response in a human bioassay;
(e) being essentially insoluble in aqueous solutions.

Isolated

In the context of this specification, the term isolated refers to the biological polysaccharide compound being isolated from a natural state such as from a cell or cell wall to a purified form. The exact method of isolation may vary but may comprise various steps to wash and remove impurities such as proteins and lipids.

The isolated biological polysaccharide compound may be substantially intact. That is, the process of isolation minimises or avoids breaking of chemical bonds in the compound and keeps the complexity and size of the biological polysaccharide compound intact. Complexity in this case may relate specifically to the ratio of branched 1:3 to 1:6 side chains of the biological saccharide compound.

Biological Polysaccharide Compound

As noted above, isolated biological polysaccharide compounds are described herein.

In one embodiment, the biological polysaccharide compound described is derived from yeast. The biological polysaccharide compound may be derived from yeast cells. The yeast cell may be from the species *Saccharomyces cerevisiae*.

The biological polysaccharide compound may be a glucan compound. The biological polysaccharide compound may be β-glucan compound.

Insoluble

The biological polysaccharide compound is insoluble in aqueous solutions.

Solubility may be defined as the maximum concentration of a substance that may be completely dissolved in a given solvent at a given temperature and pressure. The solubility of a substance may be described in a variety of ways. The USP/NF generally expresses the solubility in terms of the volume of solvent required to dissolve 1 gram of the drug at a specified temperature. Using this measure, the biological polysaccharide compound described is practically insoluble or insoluble and parts of solvent needed for one part solute is greater than 10,000.

As may be understood from the method of manufacture described further below, the biological polysaccharide compound described herein may be subjected to many aqueous washing steps during manufacture to arrive at the isolated form. Any soluble compounds or residues would be removed from the insoluble finished compound during manufacture.

Biological Polysaccharide Compound

The biological polysaccharide compound may be characterised by a specific glycosyl compound. Glycosyl chains may be the part of biological polysaccharide compound that causes an inflammatory reaction in humans. It is understood by the inventors that the isolated biological polysaccharide compound described may have numerous glycosyl side chains and these comprise exposed antigenic regions in the glycosyl chains.

The biological polysaccharide compound as noted above is unique in that it has a considerable amount of 1:6 linked glucopyranosyl residue. Art β-glucan compounds often have this side chain (and other side chains removed) to leave a very high proportion of 1:3 side chain. The inventors have found that preserving the 1:6 side chain (and others in the branched vs unbranched form) may be very important to achieving the desired efficacy.

Further the inventors have found that the biological polysaccharide compound delivers an optimal level of immune response to achieve efficacy, without having any components left within the yeast cell which may cause infection or undesired affects when placed in an open wound

Side Chain Analysis

In one embodiment, the biological polysaccharide compound described comprises only the 1:3 and 1:6 side chains described.

In an alternative embodiment, further side chains may be present besides the 1:3 and 1:6 side chains described. If present, the additional side chains may comprise at least one of the following side chain types:

1:4 linked glucopyranosyl residue;
3:4 linked glucopyranosyl residue;
2:3 linked glucopyranosyl residue;
3:6 linked glucopyranosyl residue;
2:6 and 4:6 linked glucopyranosyl residue;
3:4:6 linked glucopyranosyl residue;
terminal linked glucopyranosyl residue.

The amounts of these additional side chains may be variable. In one embodiment, they may be present (all or some or one) at the following approximate concentrations (weight %):

1:4 linked glucopyranosyl residue 2-6%
3:4 linked glucopyranosyl residue 0.01-0.5%
2:3 linked glucopyranosyl residue 0.5-4%
3:6 linked glucopyranosyl residue 3-10%
2:6 and 4:6 linked glucopyranosyl residue 0.2-1%
3:4:6 linked glucopyranosyl residue 0.01-0.5%
Terminal linked glucopyranosyl residue 2-8%

In one embodiment, the biological polysaccharide compound may be characterised by having a glycosyl compound analysis of approximately (weight %):

1:3 linked glucopyranosyl residue 67.7%
1:6 linked glucopyranosyl residue 12.7%
1:4 linked glucopyranosyl residue 4.4%
3:4 linked glucopyranosyl residue 0.3%
2:3 linked glucopyranosyl residue 2%
3:6 linked glucopyranosyl residue 6.3%
2:6 and 4:6 linked glucopyranosyl residue 0.6%
3:4:6 linked glucopyranosyl residue 0.2%
Terminal linked glucopyranosyl residue 5.8%

Whilst not being bound by theory, it is envisaged by the inventors that the presence of the 1:6 side chain in particular (and possibly the other side chain(s) noted) may be important to achieve the strong immunogenic response observed for the biological polysaccharide compound yet, not the potentially uninhibited inflammatory cascade observed as noted in the art for existing biological polysaccharide compounds such as β-glucan compounds.

Purity

The above biological polysaccharide compound may be characterised by being extremely or ultra-pure. Purity in this context refers to removal of cell constituents e.g. proteins, enzymes, lipids, nucleic material from the β-glucan and in addition all residues from the extraction process.

As noted above the purity may be from 85-100% (wt.) β-D-glucan. The purity may also be 90-100%, or 95-100% β-D-glucan.

The purity may also be measured in terms of protein or lipid impurity content.

In one embodiment, the biological polysaccharide compound may be characterised by having less than or equal to 3, or 2, or 1, or 1, or 0.5% wt protein content. In one embodiment, the residual protein content in the biological polysaccharide compound may be less than 0.3%. Residual protein content may be measured via amino acid analysis.

Further, the biological polysaccharide compound may be characterised by having less than or equal to 3, or 2, or 1 or 0.5% wt. lipid content. In one embodiment, the residual lipid content in the biological polysaccharide compound may be less than 0.3%. Residual lipid content may be measured via gravimetric extraction.

In one embodiment, the biological polysaccharide compound may be characterised as having virtual no residue from, any solvents or chemicals utilised in its extraction The purity described may be a significant advantage over the art as it allows for consistency of dosage and outcome and may avoid side indications and variation in efficacy associated with varying purity and presence of other compounds. Biological polysaccharide compounds and in particular, β-glucan compounds are naturally produced compounds in their natural state. Isolation to a high degree of purity overcomes art issues with variability in efficacy, confounding results and possible side effects or inflammatory cascade noted in the art, particularly for insoluble biological polysaccharide compounds such as those described herein.

Further in order to be able to achieve regulatory approval for therapeutic claims one must overcome the high degree of variability in the final compound which has been beset by previous extractions of the biological polysaccharide compound, i.e. within the prior art there is no certainty of achieving consistency of the biological polysaccharide compound to be able to claim a consistent level of efficacy and drug like characterisation to be able to achieve approval of the CMC package which forms a key component of any drug approval by a regulator.

Molecular Weight

As noted above the biological polysaccharide compound may be a large compound with a molecular weight of 0.5 to 2.2 MDa. In one embodiment, the molecular weight may be 0.5 to 2.2, or 0.6 to 2.2, or 0.7 to 2.2, or 0.8 to 2.2, or 0.9 to 2.2, or 1.0 to 2.2, or 1.1 to 2.2 or 1.2 to 2.2, or 1.3 to 2.2, or 1.4 to 2.2, or 1.5 to 2.2 MDa. This molecular weight may be measured as a distribution or average molar mass The molecular weight may be measured by gel permeation chromatography.

Bioassay

The bioassay referred to is a measure of inflammatory response caused by the biological polysaccharide compound as measured using a bioassay where the compound is tested for TNF-alpha response on human harvested macrophage cells. The biological polysaccharide compound used appears to not cause a runaway inflammatory cascade but does appear to kick start inflammation and healing The art gives examples where insoluble biological polysaccharide causes a severe inflammatory response which is not what the inventors observed for the compound described above.

Sterility

In one embodiment, the biological polysaccharide compound may be further characterised by having a very low bio-burden. In one embodiment, the compound may be sterile. In the context of this specification, the term 'very low bio-burden' or 'sterility' refers to a microbiological count of <10 cfu/g plus the absence of pathogens.

In one embodiment, the compound described meets USP51 (antimicrobial effectiveness) and USP61 (microbial limits) standards. In a further embodiment, the biological polysaccharide compound described may meet USP71 (sterility) standard.

The USP standards are standards enforced by regulatory agencies to measure sterility. One method of completing a USP71 test may be to perform growth promotion testing and assess other quality parameters to confirm that a media can support growth of the six microorganisms stated in USP 71 Sterility Tests. Then use either a closed membrane filtration method or a direct inoculation method to inoculate the media and then test containers are incubated at the appropriate temperatures for at least 14 days and any microbial growth measured. For a sample to be USP71 compliant, at the end of the incubation period there must be no evidence of growth and the drug product is given a "sterile" result indicating that no contaminating microorganism is found in the sample examined under the conditions of the test.

To exemplify this further, the biological polysaccharide compound described may be further characterised by having the following sterility criteria:

| | |
|---|---|
| TVAC | <10 cfu/g |
| Yeasts | <10 cfu/g |
| Moulds | <10 cfu/g |
| *Staphylococcus aureus* | Not detected/10 g |
| *Escherichia coli* | Not detected/g |
| *Pseudomonas aeruginosa* | Not detected/10 g |
| *Salmonella* spp. | <10 cfu/g |
| Bacterial Endotoxins | <1 EU/mg |

Microparticulate

The biological polysaccharide compound may be in micro-particulate form. The particle size may be less than 40 μm. This may be as measured using a Malvern particle size test method.

Presenting the isolated biological polysaccharide compound as a microparticulate may be useful to increase surface area and expose more of the antigenic regions of the biological polysaccharide compound (mainly 1-3 and 1-6 glycosyl side chains).

Appearance

The isolated biological polysaccharide compound may be a white to slightly off-white colour and, in a pure form, may be a powder.

Residual Solvents

Art methods of isolating β-glucan compounds/biological polysaccharide compounds may rely on various solvents/reagents, examples including but not limited to water, chloroform, ethanol and others.

In the inventor's experience, residual solvents are virtually undetectable in the isolated biological polysaccharide compound described herein.

Stability

The biological polysaccharide compound is highly stable. In trials completed by the inventor's, the isolated biological polysaccharide compound is shelf stable for at least 1, or 2, or 3, or 4, or 5 years after storage at ambient temperature. The biological polysaccharide compound also appears to be heat stable as well. In one trial completed on behalf of the inventors, a thermogravimetric analysis was completed which demonstrated that the compound remained stable even after treatment at 220° C., a remarkably high temperature for stability.

This may be a result of the high purity and high sterility of the isolated biological polysaccharide compound and hence, why the compounds exhibits so little if any degradation when stored over time.

Method of Treatment

A method of treating the skin of a patient in need thereof by topical application of a vehicle to a wound site, the vehicle comprising a therapeutically effective amount of an isolated biological polysaccharide compound substantially as described above.

Further examples of specific methods are described more below.

Use

Use, in the manufacture of a medicament, of an isolated biological polysaccharide compound substantially as described herein, for topical treatment of the skin of a patient in need thereof.

Further examples of specific uses are described more below.

Efficacy

The inventors have found that the biological polysaccharide compound described may be the most optimal immunogenic molecule available for wound healing.

A summary of the demonstrated efficacy from two recent phase IIB double blind randomised clinical trials completed in 2020 are noted below and described further in the Examples and Figures.

Chronic Wounds

In an 82-patient randomised double blinded randomised placebo-controlled phase IIB trial, the biological polysaccharide compound demonstrated a strong signal of efficacy vs a vehicle gel including:

- a 37% adjusted difference in incidence of complete closure over placebo in the per protocol group (p=0.052);
- a 22% adjusted difference in incidence of complete closure vs placebo in the ITT group (p=0.11);

Note that a 10% difference in incidence of complete closure is considered clinically meaningful in the art.

Cosmetic Procedures

In a 40-patient phase IIB double blind placebo-controlled trial assessing the efficacy of the described biological polysaccharide compound post a fractionated laser procedure measuring skin quality and healing. The biological polysaccharide compound demonstrated a:

- 70% improvement in wrinkling versus the placebo group (P<0.04);
- 114% improvement in elastosis (P<0.13), doubles the improvement of elastosis at 28 days.

The immune-stimulating mechanism of action may be modified to suit different indications allowing multiple applications.

It is the inventor's understanding that the isolated biological polysaccharide compound identified stimulates the innate dermal immune system by mimicking a biologic threat (e.g. a yeast infection) which causes the immune system to respond via activation of the NF-kB pathway in macrophages.

Macrophages modulate and regulate wound healing response. The described biological polysaccharide compound stimulates a simple antigen response mechanism that triggers and accelerates the natural cascading of wound healing response but does not lead to an uninhibited inflammatory response. The result appears to be an unexpectedly high efficacy in regeneration of new tissue and wound closure.

The isolated biological polysaccharide compound appears to activate pattern recognition receptors on immune cells developed during human evolution to defend against pathogenic microorganisms.

The antigenic regions of the biological polysaccharide compound, e.g. yeast glucans, may be recognised by the body's macrophages as a decoy to a perceived threat, causing stimulation of toll-like receptor (TLR) 2 and dectin-1 membrane receptors on wound macrophages and signalling pathways meant to combat the threat. The decoy however, does not cause the perceived damage but the resulting macrophage activation appears to stimulate wound healing in a variety of beneficial ways.

The method is understood by the inventor's to stimulate wound macrophage activity resulting in increased phagocytosis, increased secretion of wound healing cytokines, and stimulation of angiogenesis and wound repair.

In the inventor's experience, the methods/use have no observed side effects and no measured inflammation of concern or at all contrary to what the art would suggest for insoluble biological polysaccharide compounds.

Vehicle

The vehicle may, in one embodiment, be a gel composition comprising the isolated biological polysaccharide compound. The vehicle may be a highly viscous gel. For example, the viscosity of the gel may be greater than 3000 cps. The gel may not comprise any chemical preservatives such as paraffins or traditional chemical preservatives. This may be desirable to avoid any interference or deleterious effects to an open wound. The gel may be an aqueous gel. As noted above, the biological polysaccharide compound is insoluble and hence the biological polysaccharide compound may be suspended in the gel as a microparticulate suspension.

The vehicle may also take other pharmaceutically and physiologically acceptable forms. The vehicle generally may be aqueous. The vehicle may act to suspend or retain the biological polysaccharide compound as a microparticulate suspension or as particles on a substrate until topically applied.

Examples of alternative vehicles may be creams, ointments, dressings, medical devices used to treat the skin such as devices to treat wound and burns and so on.

Biological Polysaccharide Compound Concentration/Dose

In one embodiment the vehicle may comprise less than or equal to: 0.05, or 0.06, or 0.07, or 0.08, or 0.09, or 0.1, or 0.2, or 0.3, or 0.4, or 0.5, or 0.6, or 0.7, or 0.8, or 0.9, or 1.0, or 1.1, or 1.2, or 1.3, or 1.4, or 1.5% weight isolated biological polysaccharide compound. In one embodiment the vehicle comprises 0.05 to 1.5% wt or 0.1 to 1.0% wt isolated biological polysaccharide compound.

The vehicle may be applied daily or twice daily to the wound site. The vehicle may be applied for multiple days or weeks. The administration regime may be a function of concentration of compound in the vehicle, the treatment being undertaken, the response shown by the patient among other factors. In the inventors experience, treatment regimens tend to be once or twice daily application for a time period of 5 to 14 days, or in the case of the treatment of a chronic wound, once or twice or 3 times weekly over at 12-20 week treatment period This time period may be variable.

The vehicle may be applied at home by the patient to their skin site.

The vehicle including the compound may be applied to the site as a layer from 1-5 mm thick. Over time, the layer may be absorbed into the skin.

Chronic Wound Treatments

The method/use may be used to treat a chronic wound. The chronic wound may be an ulcer. The ulcer may be a venous leg ulcer. In the inventor's experience, the biological polysaccharide compound provided an unexpected and synergistic effect in treating venous leg ulcers compared to a placebo.

In one embodiment, the inventors found that the biological polysaccharide compound described, when used to treat a venous leg ulcer in a 67 patient phase IIB double blind randomised placebo controlled trial, had a difference in incidence of complete wound closure of around 37% compared to a vehicle gel for chronic venous leg ulcers of 2-12 cm² ulcer size. this level of efficacy would arguably be superior to any competing product currently approved.

The authors also found double the percentage wound area reduction in chronic venous leg ulcers 91% via the above described biological polysaccharide compound versus 46.6% placebo. These findings are described further in the Examples below.

Cosmetic Treatments

The method/use may be a cosmetic skin treatment. In one embodiment, the efficacy of a cosmetic skin treatment may be measured in terms of cosmesis skin quality and specifically, as measured by skin elastosis and wrinkling. In the inventor's experience, the described biological polysaccharide compound had an unexpected and synergistic effect in cosmetic skin treatment.

In one embodiment, in a phase IIB 42 patient double blind placebo controlled trial for use of the gel described post a controlled burn procedure being a $CO_2$ fractionated laser procedure of the chest, the described biological polysaccharide compound gave close to double the improved skin quality post laser ablation, elastosis 75% vs 35% placebo ($p<0.01$), and wrinkling 85% vs 50% placebo ($p<0.04$)

Further or Related Effects

The above described biological polysaccharide compound may have further tissue repair and healing effects comprising one or more of the following:
 optimisation of skin healing and skin quality;
 decreasing skin wrinkling post a cosmetic procedure;
 increasing skin elastosis during healing;
 treatment of skin post fractionated and fully ablative resurfacing (known therapeutic options to improve the appearance of UV induced photo-damage, rhytidosis, dyspigmentation, and suboptimal skin texture);
 adjunctive post-procedure topically applied gel to significantly accelerate skin quality benefits.

The biological polysaccharide compound when in a gel form like that described above has applications to any cosmetic procedure involving any wound healing including healing post one or more of the following treatments/procedures:
 Incisions;
 needling;
 abrasions;
 severe chemical peels;
 skin grafts;
 invasive and light laser procedures.

The application of the gel comprising the biological polysaccharide compound may boost the clinical effectiveness of aesthetic procedures delivering accelerated skin quality and healing benefits. This is thought to be due to the biological polysaccharide compound described stimulating the body's own process for tissue regeneration and collagen production in response to the wound initiated by the underlying cosmetic procedure, whether it be laser procedure, chemical peel or incision or any other form of abrasion Method of Manufacture of the Biological Polysaccharide Compound In a fourth aspect, there is provided a method of manufacturing an isolated biological polysaccharide compound substantially as described above by the steps of:
 selecting yeast cells;
 lysing the cells and collecting the cell wall fragments;
 acidifying then heating the cell wall fragments to remove mannan and chitin;
 conducting phase separation with solvent to remove additional mannan and chitin along with proteins, glycogen and lipids;
 separating solvent and other non-polysaccharide compounds via boiling and drying;
the method comprising at least one additional water rinse step after lysing and before acidifying.

In one embodiment, lysing may occur via alkali treatment or heat treatment or both treatments. Lysing is a common technique and other methods may also be used e.g. pressure variation, sonic disruption, homogenisers, enzymes and detergents.

The method may further comprise at least one water rinse after acidifying and before phase separation. It is thought that additional water rinsing may complete additional purification but in a mild way that retains the glycosyl branched structure of the polysaccharide unlike art methods that may be harsher and lead to changes in the polysaccharide structure.

In addition to water rinsing, after acidifying and prior to phase separation, the collected mixture may also be subjected to pH change and alcohol washing. In one embodiment, the pH may be reduced to 4.0 and alcohol washed, then increased to pH 9.0 and alcohol washed, then adjusted to pH 7.0 and alcohol washed. Alcohol and water rinsing may also occur post phase separation. The alcohol used may be selected from one or more lower alcohols. Examples of alcohol may include methanol, ethanol or propanol.

The solvent used above may be an organic solvent. The solvent used may be a non-polar solvent. The solvent used may have a specific gravity of 1.0 or greater. Examples of potential solvents that may be used include one or more of the following: methyl chloroform, chloroform, dichloromethane, tetrachloroethane, carbon tetrachloride, ethyl acetate and combinations thereof. This step of solvent extraction may be completed at room temperature. It is understood that use of a solvent of this nature maybe to remove lipids from the mixture and therefore help purify the biological polysaccharide compound.

In one embodiment, the method may comprise additional steps post separation of the solvent and other compounds via boiling and drying. In one embodiment, the dried polysaccharide may be further purified through at least one additional series of solvent rinses, alcohol rinses and optionally, further water rinses before the final product is again dried. The solvent used in these additional steps may be the same as that described above used in phase separation. The alcohol used in these additional steps may be the same as that described above as well for alcohol washing. The water rinse or rinses in this additional step or steps may be done using hot water (>50° C.). The drying described may be done in one step or via several steps and using several drying techniques e.g. spray drying, oven drying, lyophilisation, vacuum drying and so on.

It should be appreciated that the above method is quite different to the nearest art such as the process described in U.S. Pat. No. 6,242,594. In U.S. Pat. No. 6,242,594, the process described is a four step process and the above described method requires a number of additional steps broadly compromised of various washing and solvent steps and additional purification and drying steps.

In terms of producing polysaccharide on a pilot or commercial scale, additional water rinse steps were added by the inventors to stop the accumulation of large amount of salt crystals. These water rinse steps may have the added benefit of removing non-polysaccharide material and providing an early-stage purification in the process. The process of water rinsing may also be important to separate branched and unbranched molecules and therefore collect a higher proportion of branches of 1-3:1-6 compound in the final isolated product.

As described above, the method described produces a compound with a fundamentally different structure (and efficacy) than that described in the prior art. For example, the method described herein results in an isolated biological polysaccharide compound with:

A substantially higher molecular weight than the art (in the order of great 0.7-2.2 m Daltons vs a molecular weight of 60 k to 250 k Daltons (mean of 140 k Daltons) as described in U.S. Pat. No. 6,242,594;

A larger and more complex molecule consisting of a greater proportion of branched 1-6 side chains;

U.S. Pat. No. 6,242,594 teaches of producing a compound comprising 96%-97% 1-3 chain and with 3-4% 1-6 chain. The compound isolated from the method and described herein has a much larger proportion of branched 1-3 and 1-6 linkages vs unbranched 1-3 and 1-6 side chains;

The isolated compound produced by the method described here produces an ultra-pure polysaccharide with less than 0.3% proteins or lipids, much higher than that described in the art generally including in U.S. Pat. No. 6,242,594;

A very low bio-burden compound where there is minimal if any extraneous cell material in the final form compound. This may be very important given that one use of the isolated compound may be for use on an open wound.

The above described isolated biological polysaccharide compound, methods of use and manufacture may, as demonstrated above, comprise a number of advantages. Examples of some advantages may include one or more of the following:

Providing an optimal immunogenic compound designed for wound healing with an optimal level of immune response and without any deleterious inflammatory affects;

Clinical validated improved healing in chronic wounds (double blind randomized placebo-controlled trials superior to gold standard therapies;

Almost 2-fold improvement in skin quality following a standard laser treatment double blind placebo controlled human trials;

The method of manufacture appears to solve existing manufacturing challenges with the ability to produce a molecule appropriately characterised which affords a measurable consistent level of efficacy batch to batch;

Proven Antibacterial properties significantly reduce infection risk;

Indications of lower itching and tightness post procedure.

The embodiments described above may also be said broadly to consist in the parts, elements and features referred to or indicated in the specification of the application, individually or collectively, and any or all combinations of any two or more said parts, elements or features.

Further, where specific integers are mentioned herein which have known equivalents in the art to which the embodiments relate, such known equivalents are deemed to be incorporated herein as if individually set forth.

WORKING EXAMPLES

The above described polysaccharide compound, methods of use and methods of manufacture thereof are now described by reference to specific examples.

Example 1

Table 1 below shows the full characterisation of the isolated biological polysaccharide compound described above.

TABLE 1

| Biological Polysaccharide Compound Characterisation | | | |
|---|---|---|---|
| Test | Test Method | Specification | Test result |
| Appearance | Visual examination | White to slightly off-white powder | Complies |
| Identification | H NMR APFP - 1023 | Complies with standard H NMR spectrum of the isolated biological polysaccharide | See example 3 |
| Assay | Total Hexose PTM26 | >90% | |
| Glycosyl linkage analysis | Analysis by gas chromatography-mass spectrometry (GC-MS) as described by Heiss et al. (2009) Carbohydr. | 65% | See example 2<br>1:3 linked glucopyranosyl residue 67.7%<br>1:6 linked glucopyranosyl residue 12.7%<br>1:4 linked glucopyranosyl residue 4.4%<br>3:4 linked glucopyranosyl residue 0.3%<br>2:3 linked glucopyranosyl residue 2%<br>3:6 linked glucopyranosyl residue 6.3%<br>2:6 and 4:6 linked glucopyranosyl residue 0.6%<br>3:4:6 linked glucopyranosyl residue 0.2%<br>Terminal linked glucopyranosyl residue 5.8% |
| Assay-Molecular Weight | Gel Permeation Chromatography | Weight Average Molar Mass Mw = 0.5-2.2 MDa | 1 MDa |
| Molecular Weight Average (Mw) | | | 1.2 |
| % Water | USP <921> Method 1c | <15% | 7.5% |
| Particle Size | Malvern Particle Sizer-APFP-1035 | <40 μm | 21 μm |

TABLE 1-continued

Biological Polysaccharide Compound Characterisation

| Test | Test Method | Specification | Test result |
|---|---|---|---|
| Bioassay | Potency Bioassay (Lonza) | | |
| | | Active result | 64 pg/mL |
| | | Control result | 3 pg/mL |
| | Ratio: active to control response | TNF(alpha) active is 1.5× above control | 21 |
| Residual Solvents | | | |
| all Solvents Impurities Test | USP<467> | <5000 ppm | <5000 pm (approx. 160 ppm) 0.22% |
| Protein | Amino Acid Analysis | <5% | 0.3% |
| Residue on ignition | USP <281> | <1% | <20 ppm |
| Heavy Metals | USP<231> | <20 ppm | 0.3% |
| Lipids | Gravimetric Extraction | <5% | 0.30% |
| Bacterial Endotoxins | Pyrogene Endotoxine Text | <1 EU/mg | <0.1 EU/mg |
| Sterility | USP<71> | Complies with monograph | Complies |
| Microbiology | Only applies if Sterility fails | | Complies |
| TVAC | | <100 CFU/g | Complies |
| Yeast | | <10 CFU/g | Complies |
| Moulds | | <10 CFU/g | Complies |
| *Staphylococcus aureus* | | Absent/10 g | Complies |
| *Escherichia Coli* | | Absent/10 g | Complies |
| *Pseudomonas aeruginosa* | | Absent/10 g | Complies |
| *Salmonella* Supp | | Absent/10 g | Complies |

Example 2

In this example, the method and results from a glycosyl linkage analysis are described used to help characterise the isolated biological polysaccharide compound described herein.

Method

For glycosyl linkage analysis, the sample (1.2 mg) was first dissolved in 400 µL of DMSO. The sample was then permethylated, depolymerized, reduced, and acetylated; and the resultant partially methylated alditol acetates (PMAAs) were analysed by gas chromatography-mass spectrometry (GC-MS) as described by Heiss et al. (2009) Carbohydr. Res. 344:915.

Permethylation was performed by two rounds of treatment with 400 µL of sodium hydroxide (15 min) and 100 µL of methyl iodide (45 min). 2 mL of water was added to quench the reaction, and the excess methyl iodide was removed by a stream of nitrogen. Following extraction with dichloromethane, water wash (3×), and solvent removal, the permethylated material was hydrolysed using 2 M TFA (400 µL, 2 h in a sealed tube at 121° C.), reduced with NaBD4, and acetylated using acetic anhydride/TFA (250 µL+230 µL, 15 min, 50° C.). The resulting PMAAs were analysed on an Agilent 7890A GC interfaced to a 5975C MSD (mass selective detector, electron impact ionization mode); separation was performed on a 30 m Supelco SP-2331 bonded phase fused silica capillary column Results From the linkage analysis results, the most abundant glycosidic linkage for glucose was 3-linked glucopyranosyl residue, larger than 6-linked glucopyranosyl residue. The ratio of 6-Glc to 3,6-Glc was about 2 to 1, suggesting an average side chainlength of 3 Glc residues, and the ratio of 3-Glc to 3,6-Glc was about 11 to 1, suggesting a side chain on every tenth backbone Glc residue on average. Table 2 below shows the linkages identified and their relative abundance.

TABLE 2

Glycosyl composition analysis

| Peak | Area %* |
|---|---|
| Terminal mannopyranosyl residue (t-Man) | 0.1 |
| Terminal glucopyranosyl residue (t-Glc) | 5.8 |
| 3-linked glucopyranosyl residue (3-Glc) | 67.7 |
| 6-linked glucopyranosyl residue (6-Glc) | 12.7 |
| 4-linked galactopyranosyl residue (4-Gal) | 4.4 |
| 3,4-linked glucopyranosyl residue (3,4-Glc) | 0.3 |
| 2,3-linked glucopyranosyl residue (2,3-Glc) | 2.0 |
| 3,6-linked glucopyranosyl residue (3,6-Glc) | 6.3 |
| 2,6- and 4,6-linked glucopyranosyl residue (2,6- and 4,6-Glc) | 0.6 |
| 3,4,6-linked glucopyranosyl residue (3,4,6-Glc) | 0.2 |

Example 3

In this example, the method and results from an NMR study are described used to help characterise the isolated biological polysaccharide compound described herein.

1H NMR sample was prepared by dissolving the invention compound sample in D6MSO and D-TFA. The sample was tested using a 400 MHz NMR instrument. Test results are shown in Table 3 and FIG. 1A below. Anomeric H1 and H6 protons signals of the backbone and side-chains were identified. The 1-3-Glc backbone to 1-6-Glc branch ratio was calculated based on NMR data. On average, side chain length was about 4 Glc residues. The ratio of 1-3-Glc to 1-6-Glc was about 10 to 1, suggesting a side chain is attached to every tenth backbone Glc residue on average.

Table 3 below shows the NMR summary output.

TABLE 3

NMR summary output

| Type of H | Chemical shift | Integration | Notes |
|---|---|---|---|
| H6SC | 3.98 | 2.7 | H6SC: H6 Side chain (Except SC-NRT) & H6 of Branching point |
| H1SC | 4.24 | 2.0 | H1SC: H1 Side chain (Except SC-NRT) |
| H1BC | 4.50 | 7.1 | H1BC: backbone chain H1 |

Figure 1B:
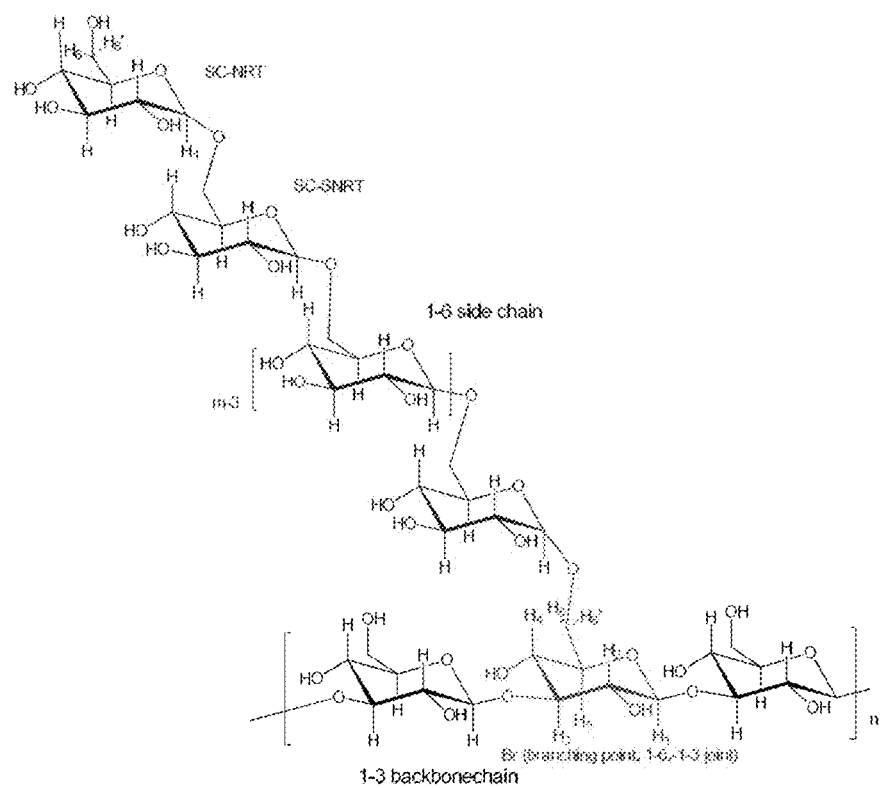

The molecule was then represented schematically as shown in FIG. 1B where the invention biological polysaccharide is a β-glucan based sugar, consisting of 3- and 3,6-linked glucose residue units. FIG. 1B shows a general structure of (1→3)(1→6)-β-glucan. For simplicity, the primary residues are labelled 'BC', 'Br' and 'SC'. While BC represent the backbone residues, Br represent the branching residues and SC represent the side-chain residues.

Example 4

In this example, a summary is provided of clinical trials completed by the applicant to date.

Over 200 patients have been studied across Phase I, phase IIA and Phase IIB clinical studies with the invention compound, most of them (over 150 subjects), in double-blind, randomized, placebo-controlled, studies. The majority of the patients have been in the USA and the rest were studies undertaken in Australia.

In recent years the applicant has completed a phase IIB clinical trial program across two indications being treatment of chronic wounds and aesthetic dermatology.

The randomised, double blinded and placebo-controlled Phase IIB chronic wound trial was completed in 2020 under FDA approved protocols and results show drug efficacy comparable if not superior to gold standard therapies.

The Phase IIB randomised double blinded placebo controlled trial on aesthetic dermatology post a $CO_2$ fractionated laser of the chest, showed an improvement in skin quality at 28 days post the procedure which was close to double that of a placebo gel.

All phase II trials have been undertaken employing FDA-approved protocol randomised trial subjects assigned to treatment or control groups using an element of chance to reduce selection and/or allocation bias.

Double-blind: neither the participants nor the administers know if they are being administered the placebo or trial treatment.

Placebo-controlled: A control group received a non-effective "placebo" treatment specifically designed to have no real effect in order to benchmark again the treatment being trialled.

Table 4 below shows a summary of the clinical validation to date.

TABLE 4

Summary of Clinical Validation Work Completed

| Phase | Indication | Country | Patients | Protocol Design | Results |
|---|---|---|---|---|---|
| Phase I/II | Venous leg ulcers | AU | 6 | Open, observational | Reduction in wound area surface vs. baseline in all patients by 35% |
| | | | 18 | Double-blind, randomised, placebo controlled | Reduction in wound surface area of 36.7% (mean) after four weeks of treatment |
| Phase IIA | Venous leg ulcers | AU | 66 | Double-blind, randomised, placebo controlled | Statistically significant ($p < 0.008$) 45% reduction in wound surface area after 85 days of treatment vs. baseline in "completer cohort" |
| Phase IIB | Venous leg ulcers | US | 82 | Double-blind, randomised, placebo controlled FDA approved | 80 patients randomised Achieved strong signals of efficacy TR-987 achieves 37% adjusted difference in incidence of complete closure over placebo in the per protocol group p = 0.052 TR-987 achieves 22% adjusted difference in incidence of complete closure vs. placebo in the ITT group (p = 0.11) Phase III powering analysis suggests statistical significance achieved at n = 300-400 patients |
| Phase IIA | Facial laser ablation | AU | Pilot - 13 Main - 26 | Double-blind, randomised, placebo controlled | Safety and feasibility established Statistically significant reduction in time to complete wound closure vs. placebo |

TABLE 4-continued

Summary of Clinical Validation Work Completed

| Phase | Indication | Country | Patients | Protocol Design | Results |
|---|---|---|---|---|---|
| Phase IIB | Facial laser ablation | US | 40 | Double-blind, randomised, placebo controlled FDA approved | ($p < 0.0062$); acceleration of wound closure by approx. 30% (mean) vs. placebo 10.9 days (Glycoprime ™ 0.1% concentration) vs. 16.3 days (placebo) 70% improvement in wrinkling versus placebo group ($P < 0.04$) 114% improvement in elastosis ($P < 0.13$), doubles the improvement of elastosis at 28 days |

Example 5

A Phase I trial was undertaken in Australia to establish safety and efficacy of the above described isolated biological polysaccharide compound. An open, non-controlled trial was conducted comprising 6 patients. The invention compound was applied topically every 2-3 days for four weeks for patients who failed standard wound therapy.

Analysis and determination of reduction in wound area by planimetry was assessed at day 56 post treatment initiation and comparison to the wound area prior to treatment. In addition safety and toxicology analysis was undertaken.

No significant intolerances or toxicities were observed or reported in association with the use of the test article. A healing response was observed in all 6 patients, with a reduction in wound surface area, measured over a 56-day period, ranging from 26% to 82%.

Figure 2:
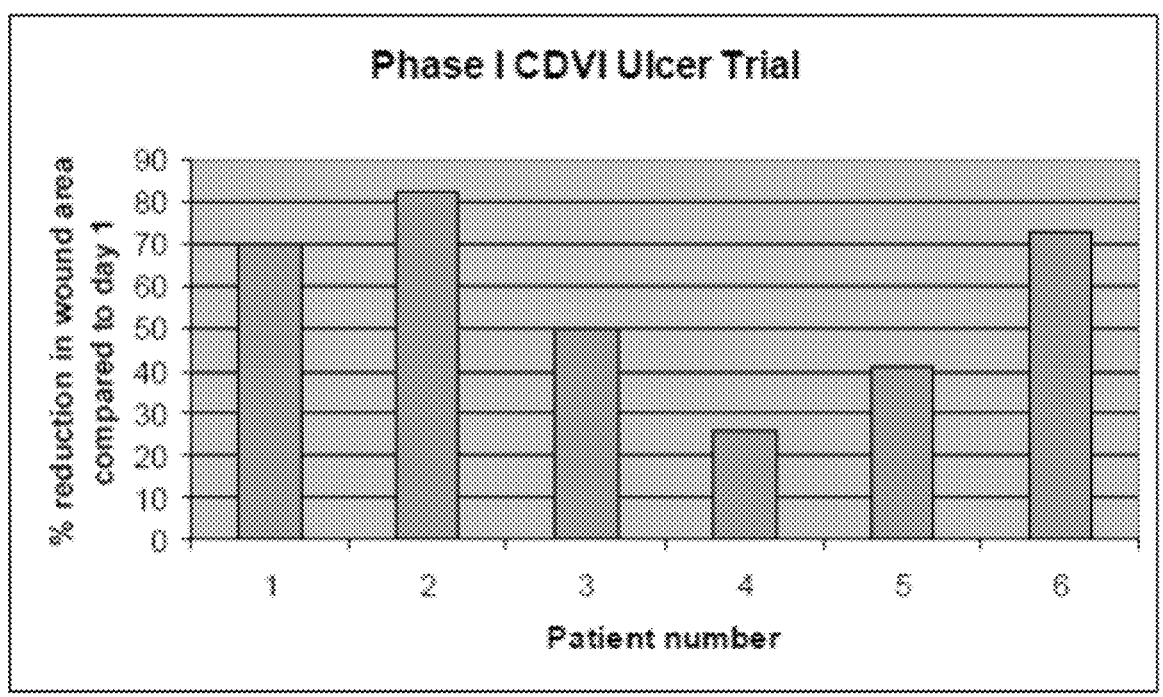
FIG. 2 illustrates the results from a phase I Australian trial to establish the safety and efficacy of a micro particulate form of the invention compound. An open, non-controlled trial was conducted comprising 6 patients. The invention compound in a vehicle was applied topically every 2-3 days for four weeks for patients who failed standard wound therapy. No significant intolerances or toxicities were observed or reported in association with the use of the test article. A healing response was observed in all 6 patients, with a reduction in wound surface area, measured over a 56-day period, ranging from 26% to 82%.

As shown in FIG. 2, an average reduction in wound size of 56% in wound surface area was observed at day 56 compared to Day 1 of treatment.

In summary, this Phase I study confirmed the ability of the invention compound to stimulate healing within chronic trophic ulcers.

Example 6

In this example, a phase I/II trial is described.

A second Phase I/II study was conducted determining the efficacy of the invention compound was studied in a single-centre, randomized, double-blind, vehicle-controlled trial in 18 patients with CDVI ulcers that had become refractory to standard wound management therapies. The invention compound was compared to another form of glucan (Glucodine™) with a lower molecular weight range and a smaller proportion of (1-6)-β-glucan side-branching and to the vehicle (control).

The two types of glucan material (invention and Glucodine™) were suspended in a cream base (0.1% w/w; paraben-preserved).

Patients were randomly assigned to the three treatment groups (two active groups and one vehicle control group), with 6 patients per group.

Treatment was 3 times weekly for 4 weeks.

No intolerances or toxicities were observed or reported in association with the use of either of the active test articles or vehicle control.

Figure 3:
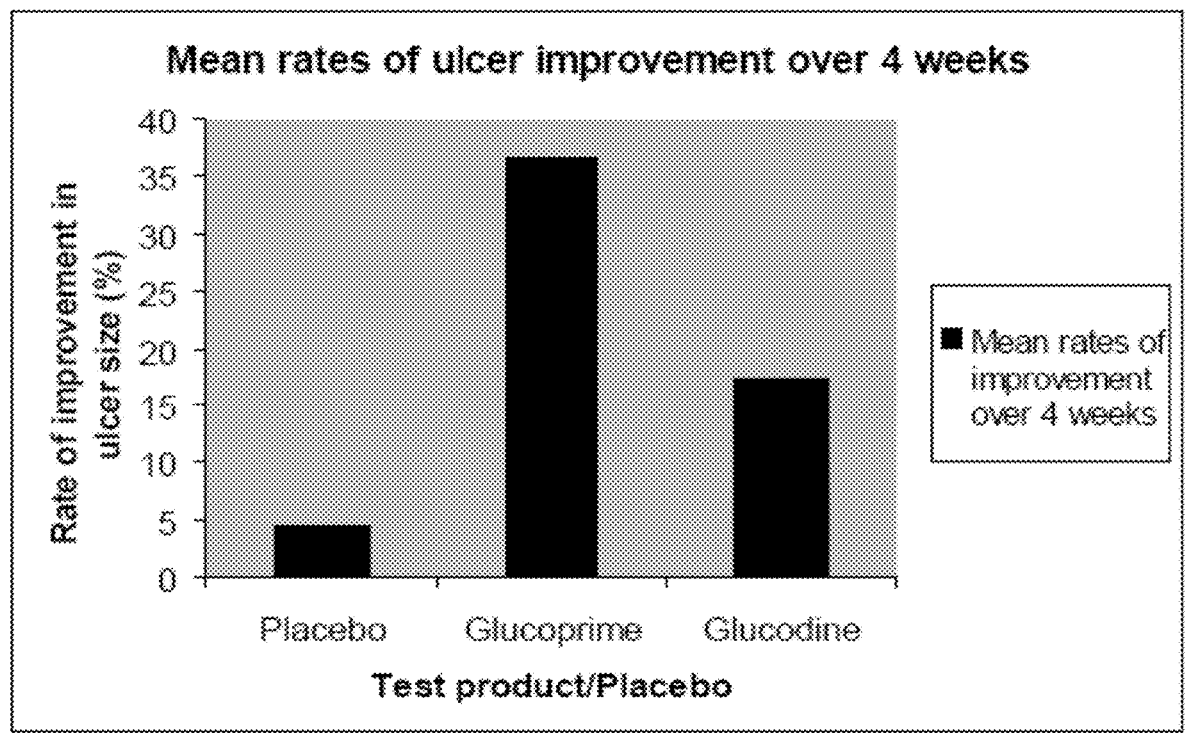
FIG. 3 illustrates the results from a second Phase I/II study which was conducted determining the efficacy of the invention compound in a single-centre, randomised, double-blind, vehicle-controlled trial in 18 patients with CDVI ulcers that had become refractory to standard wound management therapies. The invention compound was compared to another form of glucan (Glucodine™) with a lower molecular weight range and a smaller proportion of (1:6)-β-glucan side-branching and to the vehicle (control). Efficacy was assessed by planimetry, measuring the surface area of the wound. The mean rates of improvement over 4 weeks were 4.4% in the vehicle group, 36.7% in the invention compound group, and 17.3% in the Glucodine™ group. The results indicated that the invention compound contained the more efficacious active agent for the promotion of wound healing.

Efficacy was assessed by planimetry, measuring the surface area of the wound. The primary efficacy parameter was the improvement in ulcer surface area from baseline (visit 1) to the end of the trial (visit 6). The mean rates of improvement over 4 weeks were 4.4% in the vehicle group, 36.7% in the Invention compound group, and 17.3% in the Glucodine™ group. The degree of healing over eight weeks was as shown in Table 5 below and FIG. 3 (note that the invention compound is labelled 'Glucoprime' in FIG. 3).

TABLE 5

Summary of Clinical Validation Invention Compound in Phase I/II trial, mean rates of ulcer improvement over 4 weeks

|  | % Reduction in Wound Surface Area |
|---|---|
| Placebo Compound | 4.4% |
| Invention Compound | 36.7% |
| Glucodine ™ | 17.3% |

The results indicated that the invention compound was significantly more efficacious as a wound healing agent.

Example 7

In this example a phase 2A trial is described to use of the invention compound to treat a chronic wound, in this case being a venous ulcer.

A change in formulation was driven by a strategic decision to avoid preservatives such as paraben (used in the second clinical study) which had the potential to be inhibitory to macrophages. It was decided to return to the methanol preservative used in the first clinical study. Formulation studies then were conducted that led to the decision to use a gel base preserved with varying degrees of a preservative agent.

Preparations were tested containing 0.1 and 1.0% active.

This was a Phase 2, double-blind, randomized, vehicle-controlled study with patients assigned to one of the three treatment groups on a randomized basis using a computer-generated allocation sequence. Fifty-eight patients (36 males and 22 females) with chronic venous ulceration were recruited at two sites and randomly assigned to either high-dose active (1.0% invention compound gel) or low-dose active (0.1% invention compound gel), or gel base alone (vehicle control). The patients' ages ranged between 34 and 93 years, with comparable demographic characteristics across the three treatment groups. The treatment was applied three times weekly, for 12 weeks, to a depth of approximately 3 mm over the entire wound surface at the time of standard wound care management. The study was intended to provide a statistical assessment of the efficacy and safety of the invention compound in patients with chronic venous insufficiency ulcers of the leg.

As part of the study, ulcers were cleaned, debrided, the test product applied, and the wounds dressed with pressure bandages three times weekly for up to 12 weeks. The wound edges were traced weekly, and both the rate of healing and the degree of healing determined.

No drug-related toxicity was encountered during the trial in either of the active groups.

The data from the Phase II study showed that the invention compound promoted the rate at which wounds healed, with invention compound-treated ulcers healing at a statistically significant rate of improvement compared to placebo-treated ulcers. The rates of wound closure found in the study were as follows in Table 6 below.

TABLE 6

Rates of wound closure found in the study

| Group | Rate of Wound Closure | Observed Significance Level (P-Value) in Comparison to Placebo Group |
|---|---|---|
| Placebo | 5.4 mm$^2$/week | — |
| 0.1% Invention Compound | 20.4 mm$^2$/week | 0.01 |
| 1.0% Invention Compound | 15.4 mm$^2$/week | 0.04 |

The overall mean level of healing over the 12 weeks, measured by the reduction in the surface area of the ulcer, was as follows in Table 7 below.

TABLE 7

Measured by the reduction in the surface area of the ulcer

| Group | Percent Reduction in Wound Surface Area |
|---|---|
| Placebo | 10% |
| 0.1% Invention Compound | 59% |
| 1.0% Invention Compound | 55% |

Figure 4:
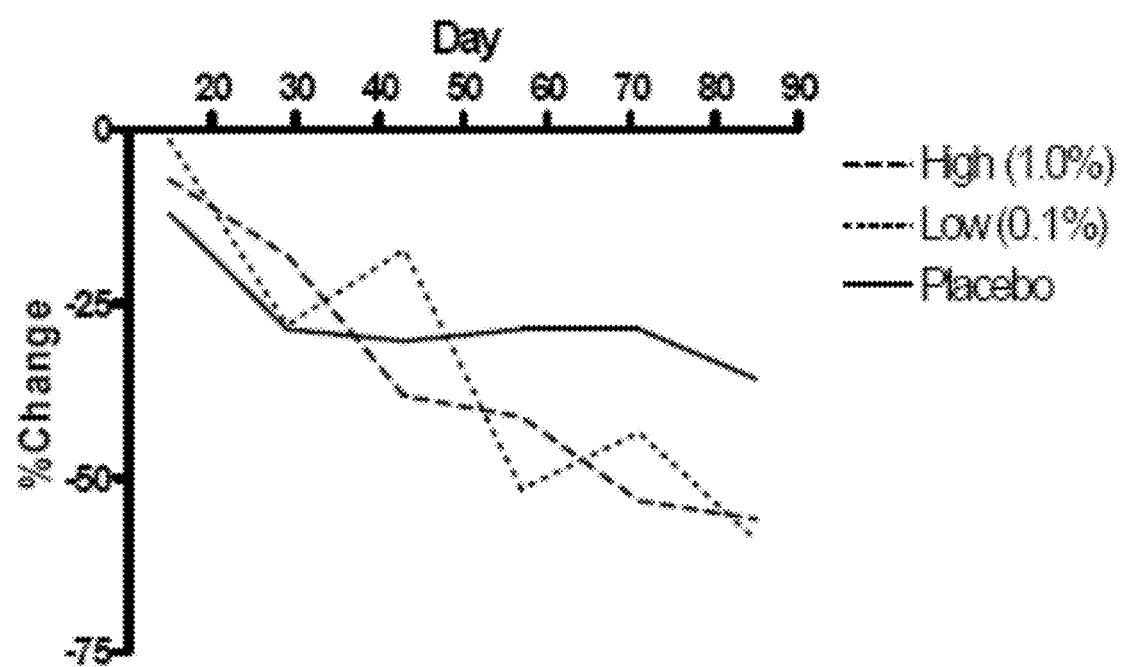
FIG. 4 illustrates the results of a third study phase IIA study which was conducted with the aim of identifying an appropriate formulation that would form the basis of a final regulatory Phase II study at the time. This was a Phase 2, double-blind, randomised, vehicle-controlled study with patients assigned to one of the three treatment groups on a randomised basis using a computer-generated allocation sequence. Fifty-eight patients with chronic venous ulceration were recruited at two sites and randomly assigned to either high-dose active (1.0% invention compound gel) or low-dose active (0.1% invention compound gel), or gel base alone (vehicle control). The study was intended to provide a statistical assessment of the efficacy and safety of the invention compound in patients with chronic venous insufficiency ulcers of the leg. The data from the phase II study showed that the invention compound promoted the rate at which wounds healed, with -treated ulcers healing at a statistically significant rate of improvement compared to placebo-treated ulcers. The invention compound demonstrated mean wound area reduction of between 55%-59% vs a placebo at 10%.

The median percent change from baseline in ulcer area is also shown in FIG. 4 where 'high (1.0%)' refers to the high dose sample and 'low (0.1%)' refers to the low dose sample.

These results were observed even though there was a large discrepancy in the size of the ulcers, with the two invention compound treatment groups having substantially larger average ulcer size than the placebo group, despite the patients being randomized.

Example 8

The full summary results from the phase IIA trial are shown below in Table 8.

TABLE 8

Phase 2A Australian Chronic Venous Ulcer Trial Results

| Treatment group | Day | Summary Statistics | | | | | Change from baseline | | | | | P-value* |
|---|---|---|---|---|---|---|---|---|---|---|---|---|
| | | n | Mean | SD | Min | Median | Max | n | Mean | SD | Min | Median | Max | |
| High (1.0%) | Day 1  | 14 | 2925.0 | 2957.69 | 50 | 2077.5 | 7470 |    |         |         |        |        |      |         |
|             | Day 15 | 13 | 2796.0 | 2743.47 | 0  | 2170.0 | 6940 | 13 | −273.2  | 525.18  | −1750  | −100.0 | 330  |         |
|             | Day 29 | 14 | 2264.5 | 2388.88 | 0  | 1257.5 | 6380 | 14 | −660.5  | 872.43  | −2970  | −265.0 | 110  |         |
|             | Day 43 | 14 | 2049.3 | 2209.04 | 0  | 1135.0 | 6110 | 14 | −875.7  | 1246.02 | −3810  | −295.0 | 70   |         |
|             | Day 57 | 14 | 1906.1 | 2190.01 | 0  | 982.5  | 6600 | 14 | −1019.0 | 1384.20 | −4370  | −420.0 | 550  |         |
|             | Day 71 | 14 | 1821.4 | 2354.15 | 0  | 900.0  | 7740 | 14 | −1104.0 | 1783.44 | −5600  | −570.0 | 1690 |         |
|             | Day 85 | 14 | 1772.1 | 2298.19 | 10 | 910.0  | 7420 | 14 | −1153.0 | 1952.62 | −6090  | −305.0 | 1370 | 0.022** |
| Low (0.1%)  | Day 1  | 15 | 3122.7 | 8955.68 | 20 | 470.0  | 35290 |   |         |         |        |        |      |         |
|             | Day 15 | 14 | 3098.6 | 8652.29 | 20 | 505.0  | 32980 | 14 | −196.4  | 674.11  | −2310  | −30.0  | 540  |         |
|             | Day 29 | 15 | 2832.7 | 8646.40 | 0  | 300.0  | 33960 | 15 | −290.0  | 504.83  | −1550  | −90.0  | 210  |         |
|             | Day 43 | 15 | 2580.7 | 7830.58 | 0  | 320.0  | 30760 | 15 | −542.0  | 1183.33 | −4530  | −140.0 | 130  |         |
|             | Day 57 | 15 | 2045.0 | 5976.54 | 0  | 340.0  | 23470 | 15 | −1078.0 | 3005.95 | −11820 | −190.0 | 30   |         |
|             | Day 71 | 15 | 1815.3 | 5388.46 | 0  | 320.0  | 21060 | 15 | −1307.0 | 3616.45 | −14230 | −220.0 | 10   |         |
|             | Day 85 | 15 | 1694.7 | 4902.60 | 0  | 320.0  | 19230 | 15 | −1428.0 | 4093.14 | −16060 | −200.0 | 90   | 0.008*** |
| Placebo     | Day 1  | 15 | 2138.2 | 4409.56 | 20 | 320.0  | 15640 |   |         |         |        |        |      |         |
|             | Day 15 | 15 | 2562.5 | 5380.42 | 0  | 250.0  | 17610 | 15 | 424.3   | 1164.90 | −100   | −20.0  | 4200 |         |
|             | Day 29 | 15 | 3598.0 | 7604.69 | 0  | 130.0  | 23890 | 15 | 1459.8  | 3370.69 | −190   | −20.0  | 10800 |        |
|             | Day 43 | 15 | 3752.0 | 9478.68 | 0  | 170.0  | 35900 | 15 | 1613.8  | 5252.51 | −540   | −53.0  | 20260 |        |
|             | Day 57 | 15 | 3667.3 | 7931.36 | 0  | 120.0  | 29110 | 15 | 1529.1  | 3604.96 | −200   | −20.0  | 13470 |        |
|             | Day 71 | 15 | 2944.0 | 6617.59 | 0  | 150.0  | 22960 | 15 | 805.8   | 2276.02 | −1470  | −50.0  | 7320 |         |
|             | Day 85 | 15 | 3222.0 | 6890.09 | 0  | 90.0   | 24850 | 15 | 1083.8  | 2512.59 | −290   | −50.0  | 9210 |         |

*Wilcoxon rank sum test with Normal approximation;
**high (1.0% MG-36) versus placebo;
***low (0.1% MG-36 versus placebo As shown in the results above, the invention compound promoted the rate at which wounds healed. With the invention compound, treated ulcers healed at a significantly faster rate (mm$^2$ per day) compared to placebo-treated ulcers. The overall mean level of healing over the 12 weeks was 10% (placebo), 59% (low dose invention compound) and 55% (high dose invention compound).

Example 9

In this example a phase IIA burn trial is described. A U.S. study was completed being a double-blind, randomized, placebo-controlled phase 2 study to investigate the safety and efficacy of 0.1% and 1.0% topically applied invention compound (the vehicle being a gel), compared to placebo, in patients undergoing carbon dioxide laser skin resurfacing (LSR) of the lower eyelids.

Design and endpoints: The study evaluated safety and efficacy of two concentrations of invention compound gel (termed GLYC-101, 0.1% concentration, and GLYC-101, 1.0% concentration), as compared to placebo (gel base), in promoting wound healing on the lower eyelid skin of 26 subjects undergoing $CO_2$ LSR for cosmetic purposes (wrinkle reduction). The study compounds were topically applied to the ablated skin area on each lower eyelid such that the entire wound surface was covered with a layer of test article (either placebo or GLYC-101), approximately 0.5 mm thick (not to exceed 1 mm). Test article was applied each day (approximately 24 hours from the previous application) for a total of 5 days. Overall, when compared to placebo, treatment with the invention compound (GLYC-101 1.0% or GLYC-1010.1%) was safe and well tolerated.

Results: The study drug appeared to neither increase the incidence or aggravate any existing safety issues nor decrease the number or reduce the severity of safety events associated with postoperative $CO_2$ LSR ablation of the lower eyelid areas for the purpose of wrinkle removal.

Figure 5:
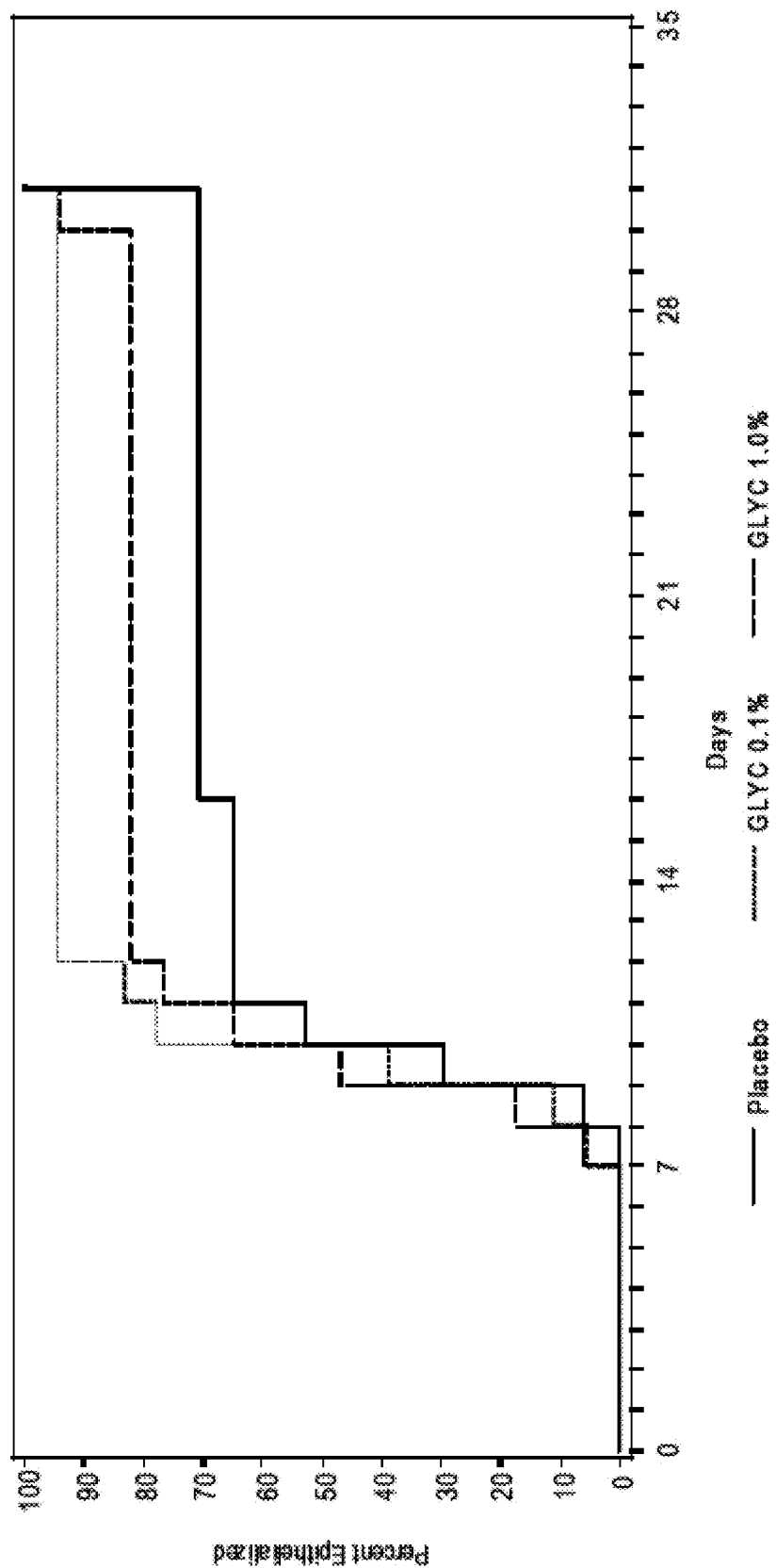
FIG. 5 illustrates the results from a 26 patient phase IIA trial from the use of a gel comprising the invention compound post a controlled burn being a fractionated cosmetic laser procedure. The study showed an average 30% improvement in time wound healing. The efficacy outcome of time to complete wound closure was more rapid when the invention compound (labelled GLYC-101 0.1% and GLYC-101 1.0%) groups were compared to placebo (p=0.0062 and 0.0331, respectively)

The comparison of each GLYC-101 (now named TR-987 the invention compound) arm to placebo with respect to the primary endpoint (time to complete wound closure) showed positive results when considering the full subject dataset from all treatment combinations. FIG. 5 shows the phase 2 trial laser data time to wound closure. Showed an average 30% improvement in time wound healing. More specifically, the efficacy outcome of time to complete wound closure was more rapid when the invention compound (GLYC-101 0.1% and GLYC-101 1.0%) groups were compared to placebo ($p=0.0062$ and $0.0331$, respectively). These results demonstrate efficacy for the invention compound.

Example 10

Figure 6:
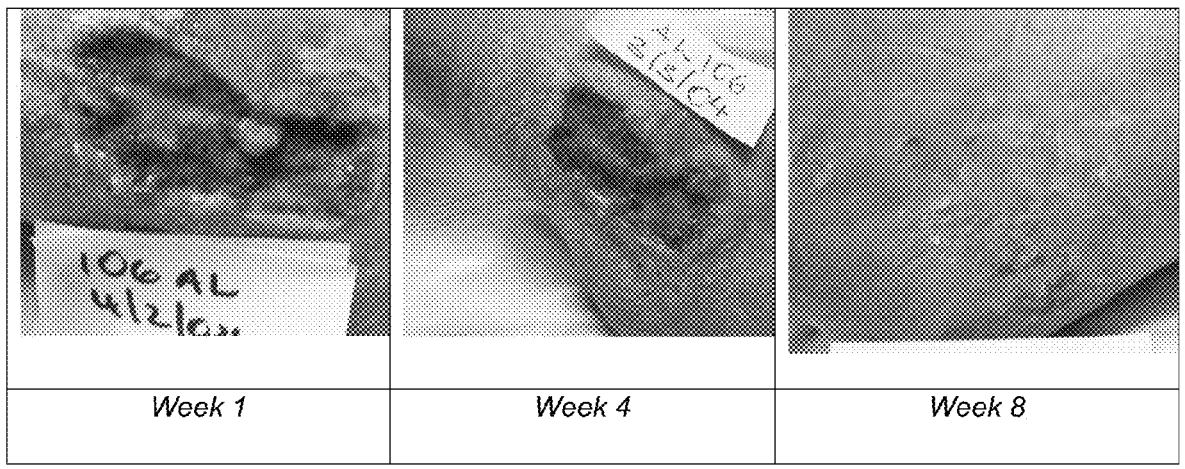
FIGS. 6, 7 and 8 illustrate photographs of atypical examples of patients wound size reduction of venous ulcers wounds in the phase IIA Australian trial completed using the invention compound.
Figure 7:
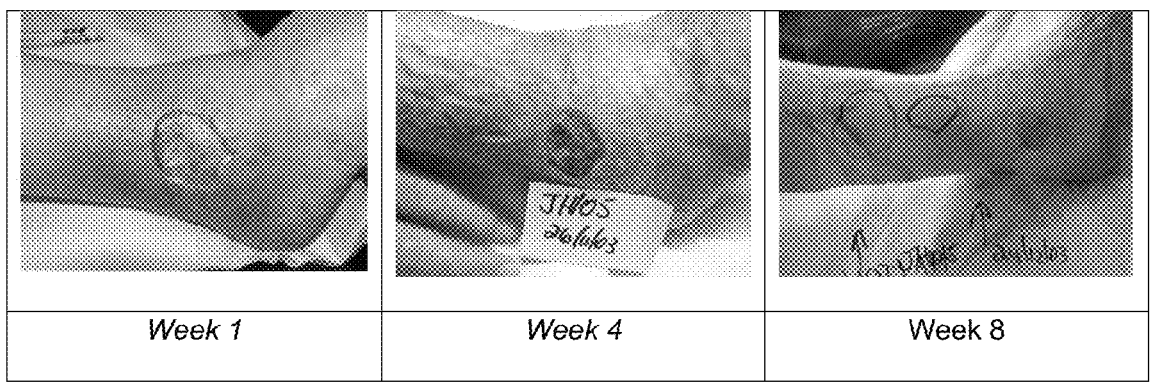
Figure 8:
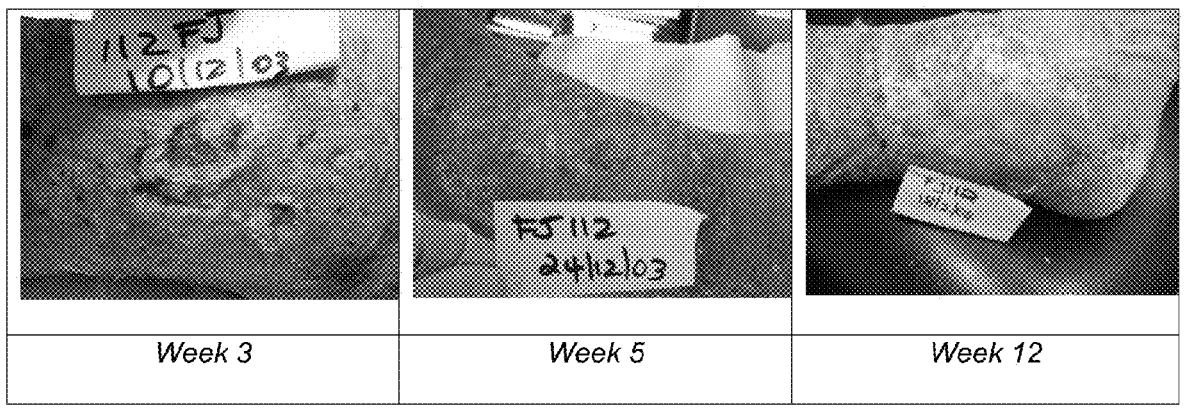

In this example, phase IIA trial results are shown with reference to FIG. 6, FIG. 7 and FIG. 8.

Specifically, in FIGS. 6, 7 and 8, an atypical example is shown of wound size reduction of a venous ulcer wound in the trial completed using the invention compound. Across the 58 patients in the completer cohort a statistically significant reduction of 45% was evidenced over 12 weeks ($p<0.008$) for patients receiving the invention compound.

Examples of patients receiving the invention compound treatment are shown based from an Australian venous ulcer trial. As shown in the images, the ulceration diminishes significantly over time, in the three examples shown, healing or near complete healing occurs within 8 to 12 weeks.

Example 11

In this example a trial is described illustrating wound closure findings from a phase IIb trial.

A double blind placebo controlled randomised phase IIB clinical trial phase IIB study evaluating the invention compound vs a placebo gel in the treatment of chronic venous ulcers was completed.

Overall, 82 subjects were randomised to treatment (42 invention compound, 38 placebo) and provided at least one post baseline assessment of ulcer area (the ITT population). A per protocol population was defined by the sponsor: the PP population excluded subjects if they withdrew early, had material protocol deviations or serial infections.

Key criteria of the trial included
Phase IIB venous leg ulcer trial;
The trial was ambitious and robust;
Double blind placebo controlled;
FDA approved protocol under an active IND;
VLUs treated with invention compound+standard of care being compression bandages vs versus placebo gel and the same standard of care;
Placebo gel was genuine vehicle control in disguisable from the active arm in all respects;
Recruitment at 10 US sites and 3 Australian sites;
Treatment period 12 weeks;
Treating ulcers 2-20 $cm^2$, with protocol variation examining ulcers at 2-12 $cm^2$;
A run in period was part of the inclusion criteria such that fast healers exhibiting more than a 30% reduction were excluded from randomisation to ensure only poorer healing ulcers were included in the trial;
No age limit on the ulcers some ulcers enrolled were persistent some 300 weeks prior to randomisation.

The analysis indicated that although the primary objective of time to heal showed no difference between the group, the key secondary objectives in the proportion of wounds 100% healed showed a robust signal of efficacy. Proportion of wounds achieving 100% closure is considered a gold standard FDA endpoint for would healing.

In summary the key initial analysis around incidence of wound closure and wound area reduction between active and placebo identified that there was in the trial:
A 21% adjusted difference in incidence of complete closure ($p=0.12$) for the ITT Group (n=67) for 2-12 $cm^2$ ulcers;
A 37% difference in incidence of complete closure ($p=0.052$) for the per protocol group (n-69) 2-12 $cm^2$ ulcers;
Double the percentage wound area reduction in chronic venous leg ulcer (VLUs) 91% invention compound vs 46.6% placebo for the per protocol group ($p=0.035)^2$ 2-12 $cm^2$ ulcers.

Additional objectives around reduction in wound area also showed a strong signal of effects and reduction in overall pain compared to placebo (which was statistically significant) further showed a strong signal of efficacy.

Figure 9:
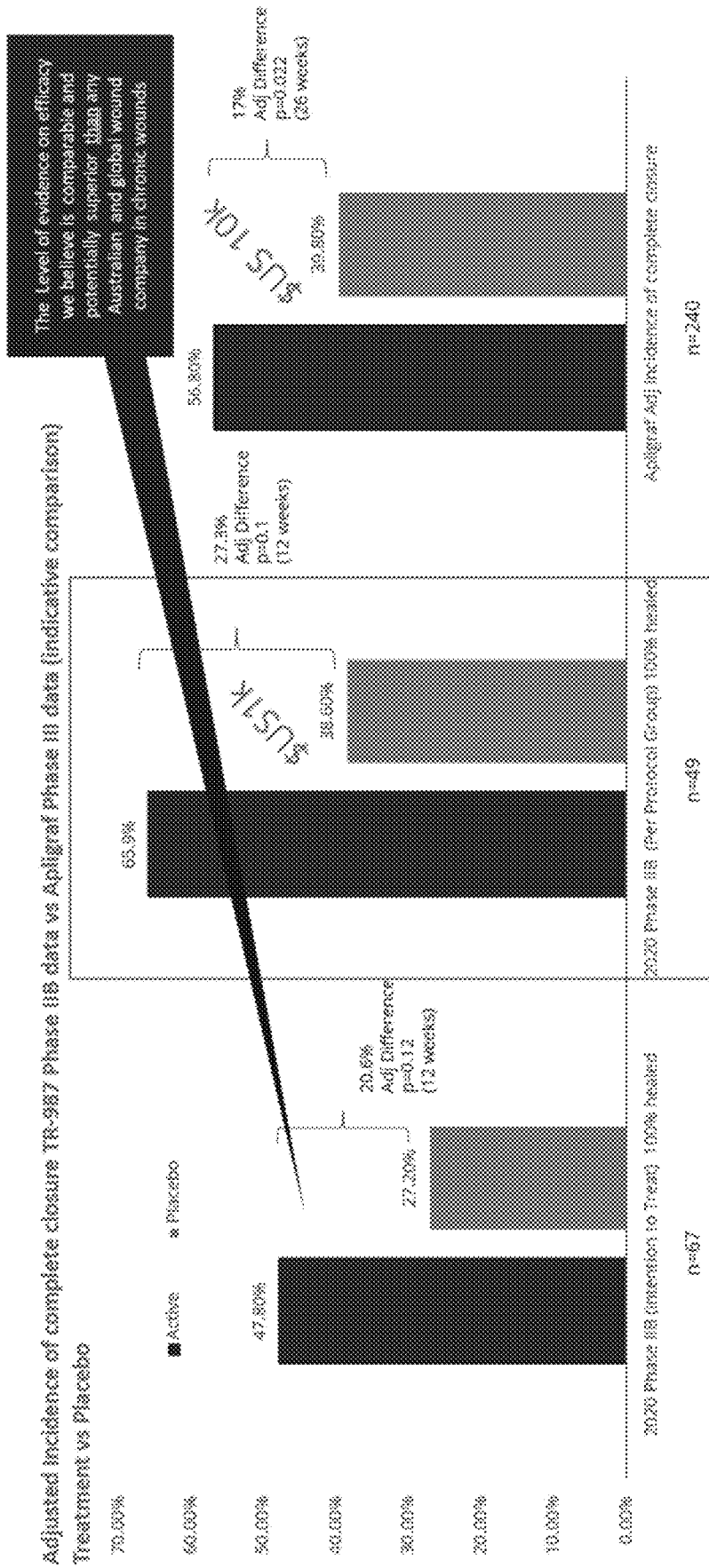
FIG. 9 illustrates the difference in the raw incidence of complete closure between vehicle and active groups for the invention compound in a USA based 82 patient phase IIB trial vs phase II data of an incumbent product Apiligraf™ and its phase III results. Apiligraf™ (see www.apiligraf.com) is arguably the gold standard for venous leg ulcer (VLU) closure being reimbursed at c$1200US per application, 3-15 applications may be needed in a normal treatment of VLU using Apiligraf™. The invention compound achieved 21% adjusted difference in incidence of complete closure vs adjusted incidence of complete closure for Apiligraf™ of 17%. Meaningful differences for the ITT group and PP groups are recorded. Results are not strictly comparable given differences in trial design (including blinding,) inclusion and exclusion criteria but provide a strong signal of comparable or superior efficacy for the invention compound over the gold standard product.

FIG. 9 shows the difference in the raw incidence of complete closure between vehicle and active groups for invention compound vs phase III data from the Apiligraf™ phase III label. Apiligraf™ is arguably the gold standard for VLU closure being reimbursed at c$1200US per application, 3-15 applications may be needed in a normal treatment of VLU.

The invention compound per protocol group from the phase IIB trial are those patients that completed the trial and received the full drug dosage over the 12-week period (the inventors consider this group is an accurate measure of efficacy for the drug).

The ITT group includes all patients who were randomized including all early withdrawals, that did not receive the full 12 weeks of treatment A clinically meaningful difference is generally considered to be +10% difference of absolute closure.

As shown in FIG. 9, the invention compound achieves 21% adjusted difference in incidence of complete closure vs adjusted incidence of complete closure for Apligraf™ of 17%. Meaningful differences for the ITT group and PP groups are recorded.

Adjusted data is based on logistic regression (invention compound) and Cox regression (Apligraf™) controlling for factors known to affect healing between the groups (e.g. base line, ulcer size etc).

Results are not strictly comparable given differences in trial design (including blinding,) inclusion and exclusion criteria but provide a strong signal of comparable or superior efficacy for the invention compound.

Figure 10:
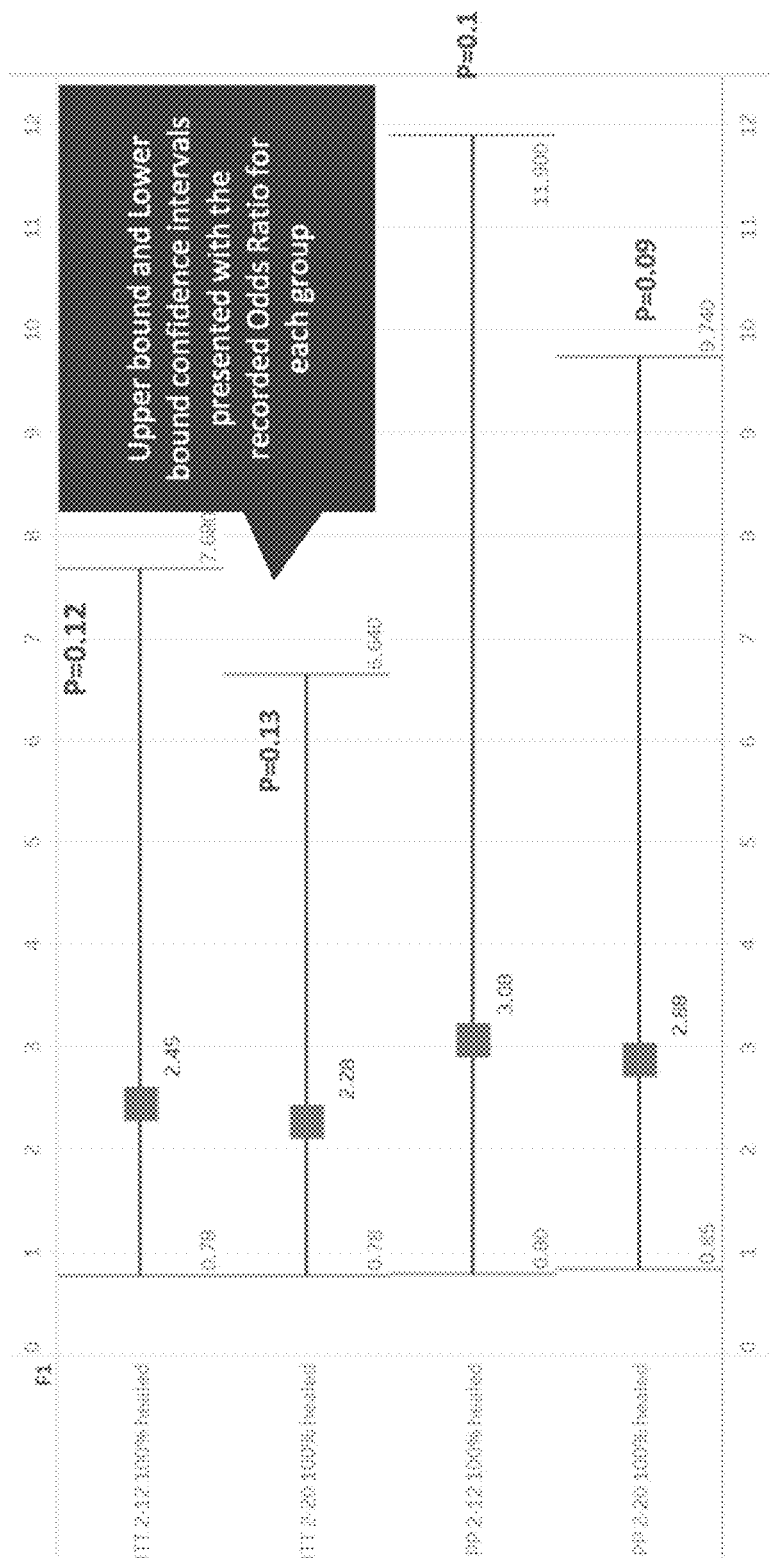
FIG. 10 illustrates; the ODDS RATIO ("OR") output from an 82 patient phase IIB trial in venous leg ulcers. It shows the OR achieving 100% healing for the active group over placebo. The output is from a logistic regression adjusting for covariates known to affect healing. The interpretation of the OR, by way of example if an OR is 1.4 the odds of healing in the TR 987 group are 1.4 times higher than the odds of healing in the placebo group. A value over 1 favours treatment and a value under 1 favours placebo. The odds ratio for all groups are clinically meaningfully (over 2.0) and all favour the invention compound which suggest the odds of achieving complete healing are 2× that in the active group over placebo.

FIG. 10 shows the recorded logistic regression Odds Ratio ("OR") of achieving 100% healing for the active group over placebo. The output is from a logistic regression adjusting for covariates known to affect healing. The interpretation of the OR, by way of example if an OR is 1.4 the odds of healing in the invention compound group are 1.4 times higher than the odds of healing in the placebo group. A value over 1 favours treatment and a value under 1 favours placebo.

The OR's recorded are all over 2 in favour of treatment which suggest the odds of healing in the active group are over 2× that of achieving complete healing in the placebo group FIG. 10 presents the OR for each of the displayed ITT and PP groups for complete healing for both size groups identified in the protocol 2-20 $cm^2$ and 2-12 $cm^2$. The upper and lower bound confidence intervals are also presented.

The odds ratio for all groups are clinically meaningfully significant and all favour treatment, as "n" increases (in a phase III trial) it is hypothesised the confidence intervals presented will narrow to achieve statistical significance. The results demonstrate you patients were over 2× more likely to achieve 100% closure in the invention compound group over the vehicle or placebo group.

Example 12

Figure 11:
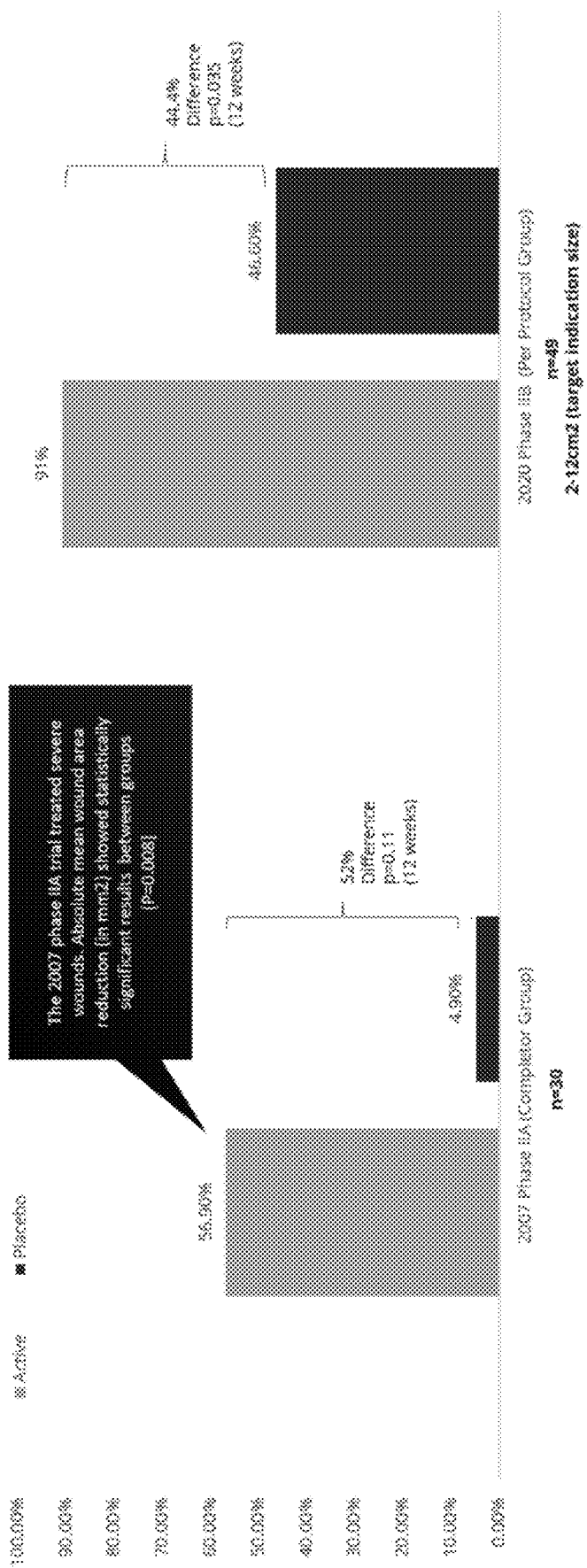
FIG. 11 illustrates a comparison of the mean wound area reduction of patients completing the phase IIA and phase IIB trials. This data demonstrates the invention compound produces a consistent efficacy as measured by wound area reduction in two separate independent phase II trials.

In this example the mean wound area reduction in phase IIA and phase IIB trials is described with reference to FIG. 11. This data demonstrates the invention compound produces a consistent efficacy as measured by wound area reduction in two separate independent phase II trials.

Mean wound area reduction is considered an acceptable endpoint by the FDA for phase II trials for measuring efficacy with respect to healing. It is considered a precursor or signal of healing and as such is accepted by the FDA as valid phase II endpoint only. It is not accepted as a valid phase II endpoint. The invention compound results per protocol group from the phase IIB trial show results for those patients that completed the trial and received the full drug dosage and the completer cohort in the phase IIA trial which are those patients that completed the trial FIG. 13 demonstrates a comparison of the efficacy of the invention using the metric of wound area reduction compared to Epifix™

Epifix™ data used was from a published sponsor funded trial (not through FDA) which was not double blinded i.e. physicians were unblinded. Epifix™ is a biologic patch similar to Apligraf™ which has been approved as a human tissue product and achieved reasonable commercialisation. Epifix™ is reimbursed at over $1000 per application, with multiple applications required for closure. More information on Epifix™ is described at https://mimedx.com/epifix/.

Figure 13:
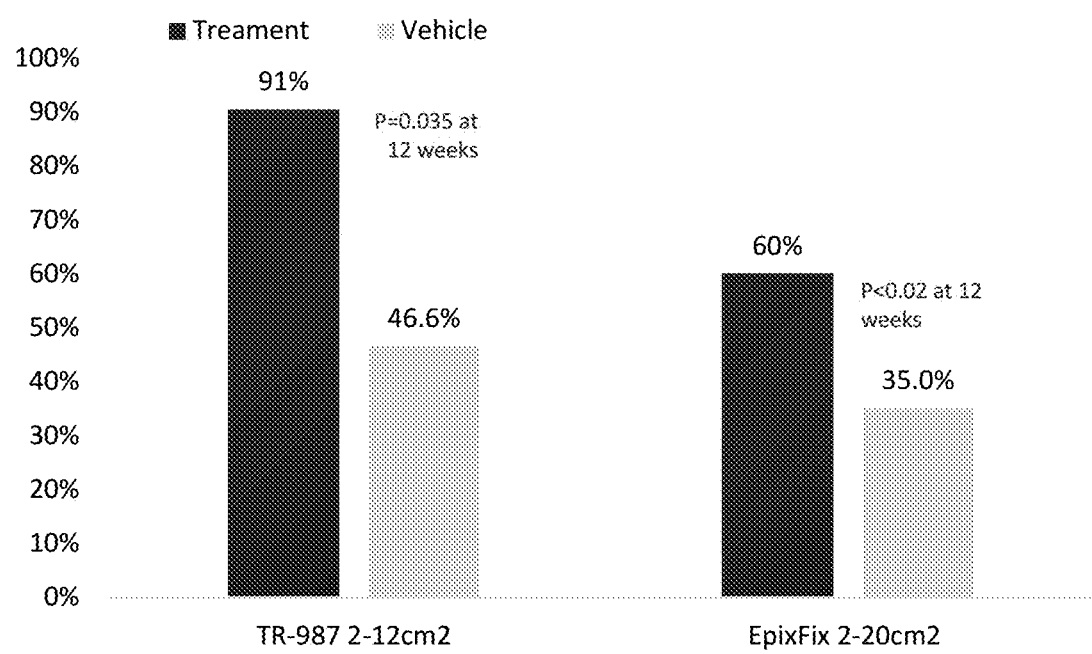
FIG. 13 illustrates a comparison of the efficacy of the invention compound using the metric of wound area reduction compared to Epifix™, a product derived from human placentas and approved as a human tissue healing product (see https://mimedx.com/epifix/)

As shown in FIG. 13, the invention compound achieves a difference in mean wound area reduction of close to double placebo 91% (labelled TR-987) vs 47% placebo, an absolute difference of 44% (p=0.035) vs Epifix™ which achieves an absolute difference of 25% between the invention compound and placebo (p<0.02).

Example 13

Figure 12:
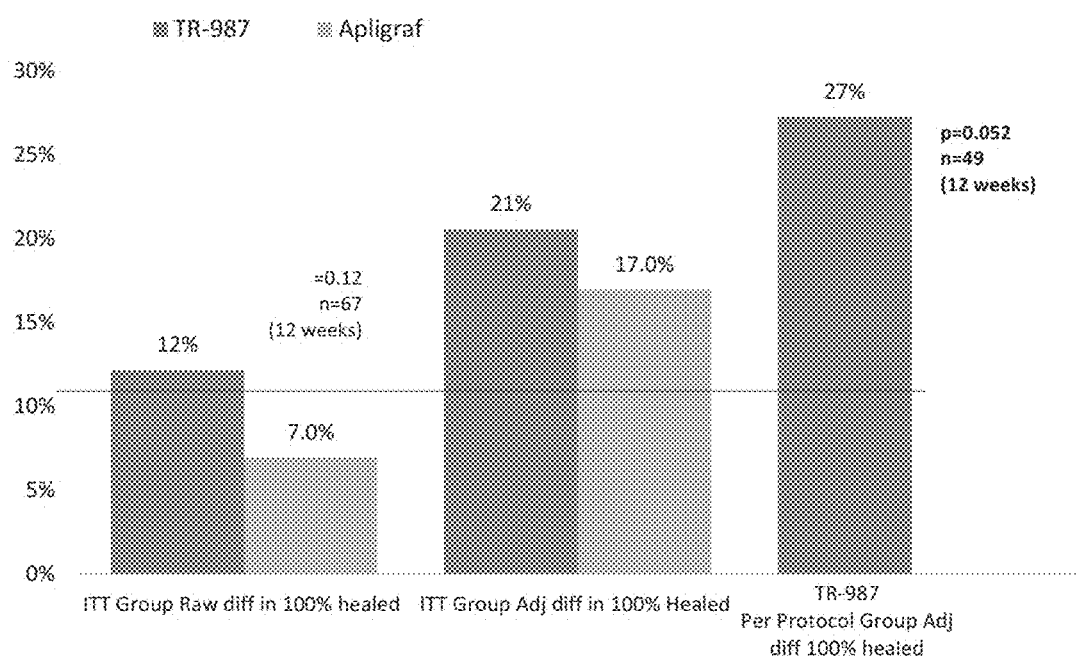
FIG. 12 illustrates the invention compound efficacy vs Apiligraf™ for venous leg ulcer treatment. It illustrates the difference in incidence of complete closure vs placebo. In this Figure, the invention compound is labelled TR-987. The Figure illustrates the difference in the proportion of patients achieving complete closure between Active and Placebo. The invention compound achieves a 21% adjusted difference in incidence of complete closure vs adjusted incidence of complete closure for Apiligraf™ of 17% illustrating superior differences of the invention compound against the arguable gold standard product.

In this example, the invention compound was compared against an art product Apligraf™ (see www.apligraf.com) for venous leg ulcer treatment (VLU). FIG. 12 shows the difference in the raw incidence of complete closure between vehicle and active groups for the invention compound vs phase III data from the Apligraf™ phase III label. Apligraf™ is arguably the gold standard for VLU closure being reimbursed at c$1200US per application, 3-15 applications may be needed.

The invention compound per protocol group from the phase IIB trial are those patients that completed the trial and received the full drug dosage over the 12-week period (this group is an accurate measure of efficacy for the compound).

ITT group includes all patients randomized including all withdrawals.

A clinically meaningful difference is generally considered to be +10% difference in 100% wound closure.

The invention compound achieved a 21% adjusted difference in incidence of complete closure over placebo vs adjusted incidence of complete closure for Apligraf™ of 17% over placebo illustrating superior differences to the invention compound against arguably the gold standard product across both the ITT group and PP groups.

21% adjusted difference for the invention compound (termed TR-987) study is the absolute difference of complete healing observed between TR-987 and the placebo used in that trial.

Adjusted data is based on logistic regression (invention compound) and Cox regression (Apligraf™ controlling for factors known to affect healing between the groups (e.g. base line ulcer size).

Results are not strictly comparable given differences in trial design (including blinding) inclusion and exclusion criteria but provide a strong signal of comparable efficacy for the invention compound.

Example 14

In this example, a trial comparing the invention compound and an art product Epifix™ is shown comparing wound area reduction. The percent wound area reduction invention compound (labelled TR-987) vs Epifix™ is shown in FIG. 13.

Mean wound area reduction is considered an acceptable endpoint by the FDA for phase II trials only for measuring efficacy not for phase II or pivotal trials The invention compound presents per protocol group from the phase IIB trial which are those patients that completed the trial and received the full drug dosage (this group is an accurate measure of efficacy for the drug).

Epifix™ data is a sponsor funded trial (not through FDA) which is not double blinded i.e. physician's new active vs treatment.

The invention compound achieves a difference in mean wound area reduction of close to double placebo 91% vs 47%, an absolute difference of 44% (p=0.035) vs Epifix™ which achieves an absolute difference of 25% (p<0.02).

The invention compound reduction in wound area mirrors the earlier phase IIA trial data 55% vs 25% (p<0.01).

Epifix™ is a biologic patch similar to Apiligraf™ which has been approved as a human tissue product and achieved significant market penetration. Epifix™ is reimbursed at c+$1000 per application, with multiple applications required for closure.

Results are not strictly comparable given differences in trial design, inclusion and exclusion criteria, level of patient and physician blinding but provide a strong signal of comparable efficacy for the invention compound.

Example 15

In this example, phase IIB trial results are described with reference to FIG. 14 and FIG. 15 to illustrate typical examples of a VLU wound healed with the invention compound in the phase IIB venous leg ulcer trial n=67 (2-12 $cm^2$).

Figure 14:
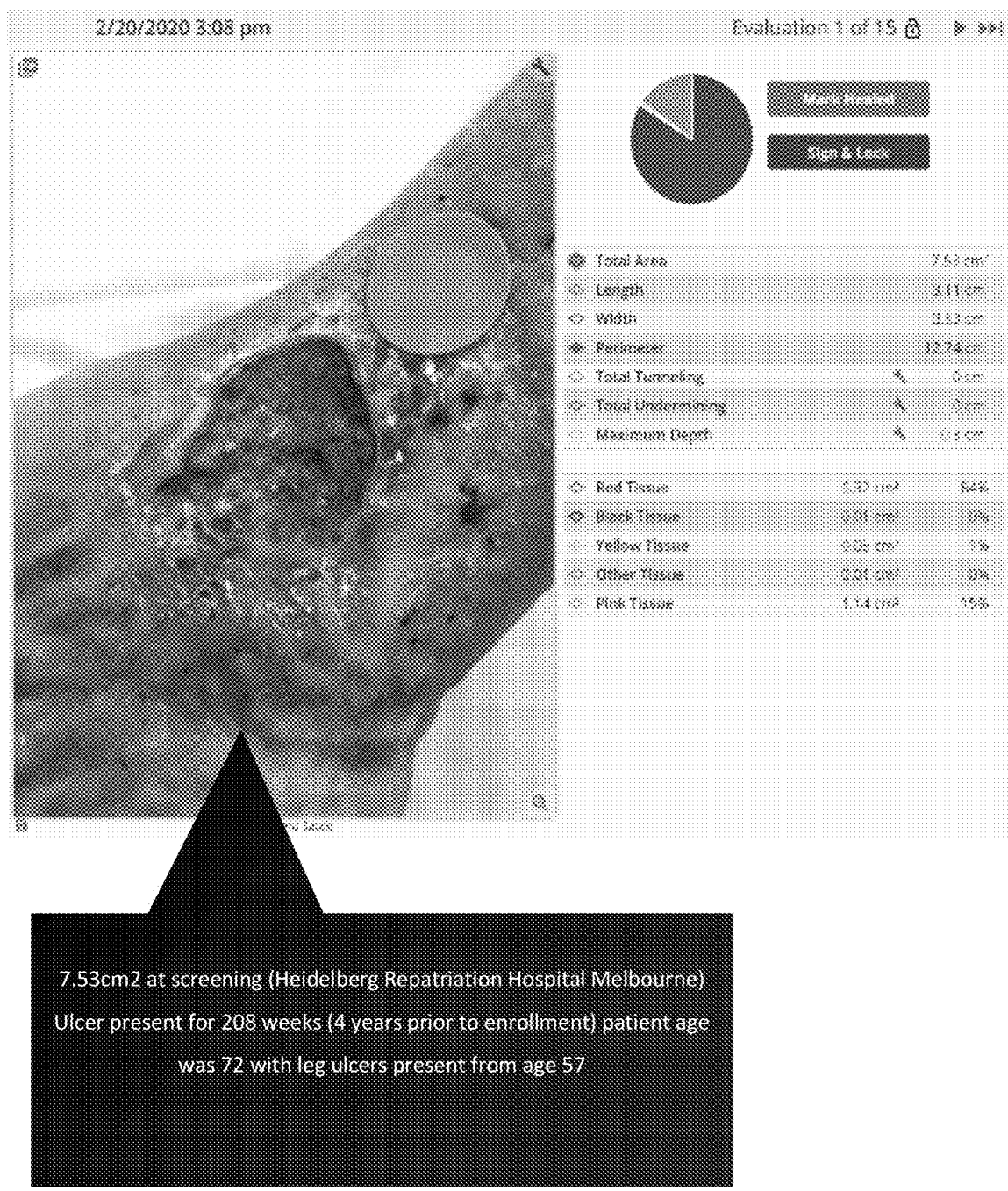
FIGS. 14, 15 and 16 illustrate atypical example photographs of patient wound size reduction of venous ulcer wounds in a phase IIB 82 patient trial completed using the invention compound.
Figure 15:
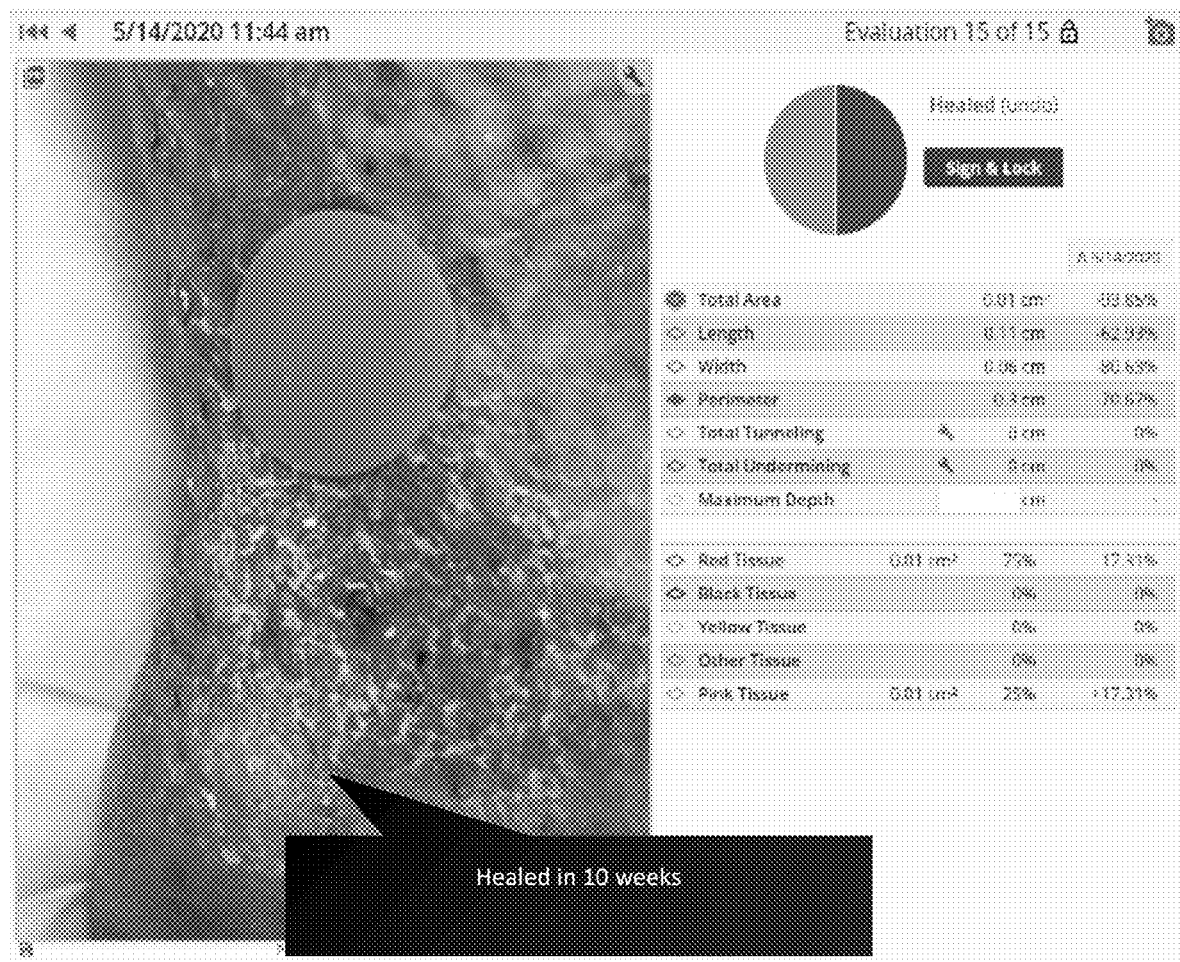
Figure 16:
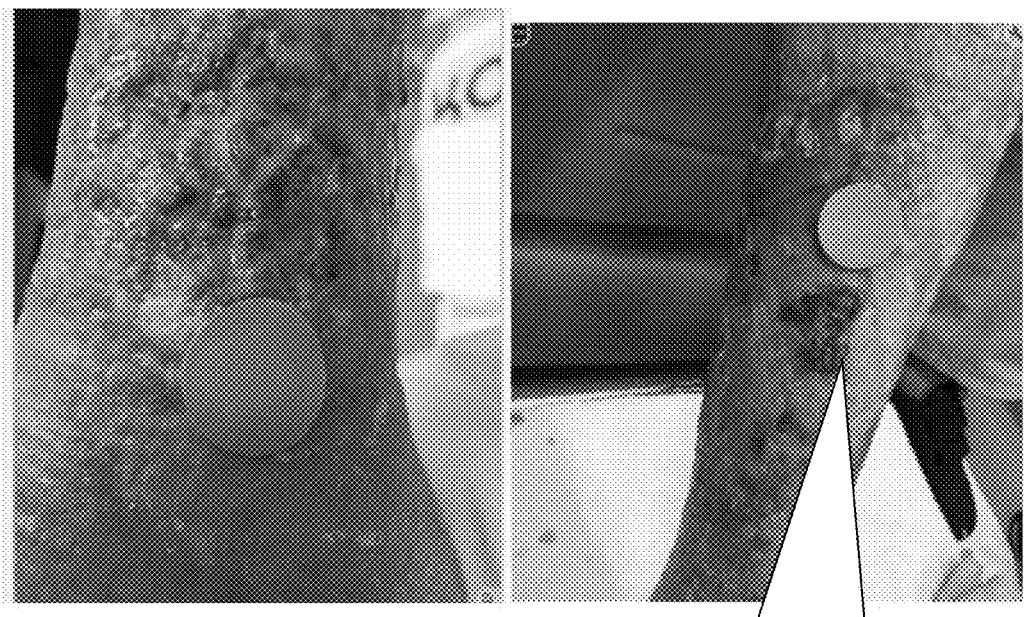

FIGS. 14 and 15 illustrates another example from the trials showing healing in 12 weeks where the ulcer size on randomization was 7.53 $cm^2$ Presented at The Heidelberg Repatriation Hospital in Melbourne Australia, The Ulcer had been open for over 4 years prior to enrolment. The Ulcer close with 10 weeks of treatment with TR-987

Example 16

The invention compound has been identified by the applicant to be a useful post procedure topical gel that close to doubles improvements in skin quality and the clinical effectiveness of cosmetic procedures at 28 days.

Figure 17:
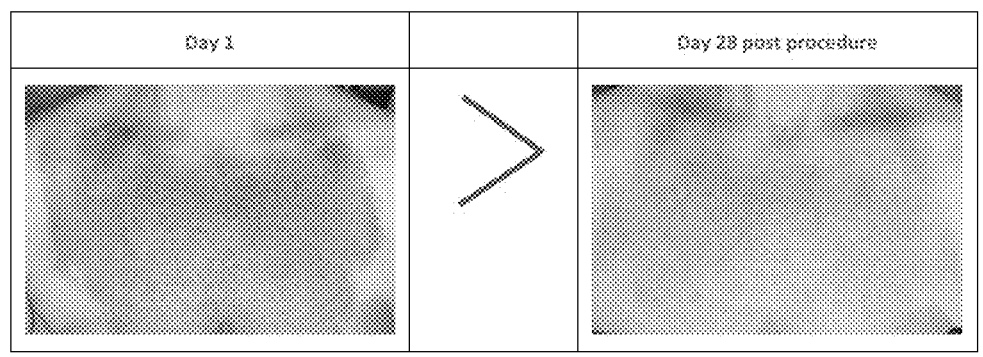
FIG. 17 illustrates an atypical example of a patient receiving the invention compound post a minimally invasive cosmetic procedure ($CO_2$ Fractionated laser procedure of the chest) and an atypical example of an improved skin quality outcome found in the phase IIB laser ablation trial n=40. Patients using the invention compound in the phase IIB trial experienced close to double the incidence of accelerated skin quality measured by elastosis and wrinkling at day 28 from the use of the invention compound in a gel vehicle vs placebo gel+standard of care (p<0.04, n=40)

FIG. 17 illustrates an atypical example of a patient receiving the invention compound post a minimally invasive cosmetic procedure ($CO_2$ fractionated laser procedure of the chest) and an atypical improved skin quality outcome found in the phase IIB laser ablation trial n=42. The image on the left shows a chest post fractionated laser procedure. The image on the right shows the same chest on day 28 post procedure and after daily treatment of the skin treated using the invention compound.

Patients using the invention compound in the phase IIB trial experienced close to double the incidence of accelerated skin quality measured by elastosis and wrinkling at day 28 from the use of the gel vs placebo gel+standard of care (p<0.04, n=40).

Ablative fractionated lasers have been increasingly utilised in recent years to improve the appearance of UV-induced photo-damage, skin wrinkles (rhytides) and scarring. Postoperative skin care is critical in promoting optimal wound healing after therapy, however there is currently no gold standard post procedural agent.

The invention compound findings in the phase IIB trial demonstrated that the invention compound generates additional collagen production and fibrosis, filling out wrinkles and fine lines at an accelerated pace.

Completed Phase IIB Trial (Post $CO_2$Fractionated Laser)

The clinical trial methodology (n=40) used above was to mimic a standardised burn wound, created by a fractionated $CO_2$ laser procedure on the full chest area. The doubled blinded/placebo controlled clinical study was conducted by a third party.

Wrinkling

Figure 18:
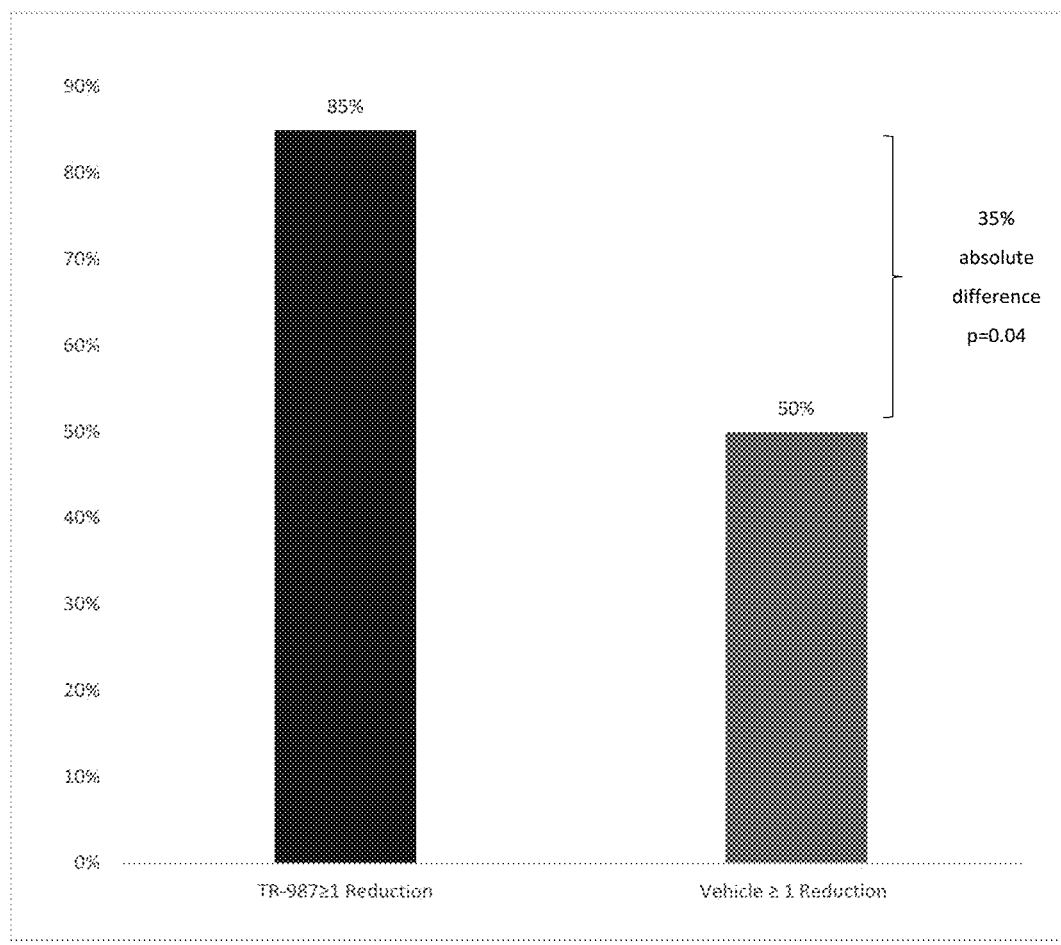
FIG. 18 illustrates the proportion of patients within each of the invention compound and vehicle groups who achieved a ≥1-point improvement in wrinkling score between baseline and day 28 (Fitzpatrick-Goldman Classification). 85% of responders achieved a wrinkling score of 1 or greater for the invention compound group versus the placebo group (where only 50% of responders achieved a wrinkling score of 1 or greater). A 70% variance P<0.04 using chi square, or Fisher exact.

FIG. 18 details the proportion of patients within each of the invention compound and vehicle groups who achieved a ≥1-point improvement in wrinkling score between baseline and day 28 (Fitzpatrick-Goldman Classification). A chi square test for unadjusted proportions was used to determine significance expressed as a p value.

85% of responders achieved a wrinkling score of 1 or greater (33% improvement) for the invention compound group versus the placebo group (where only 50% of responders achieved a wrinkling score of 1 or greater).

A 70% variance P<0.04 using chi square, or Fisher exact.

Elastosis

75% of responders achieved an improvement score of 3 or greater in elastosis (33% improvement) for the active group versus only 35% of responders for the placebo group at 28 days (a 114% variance P<0.011).

Figure 19:
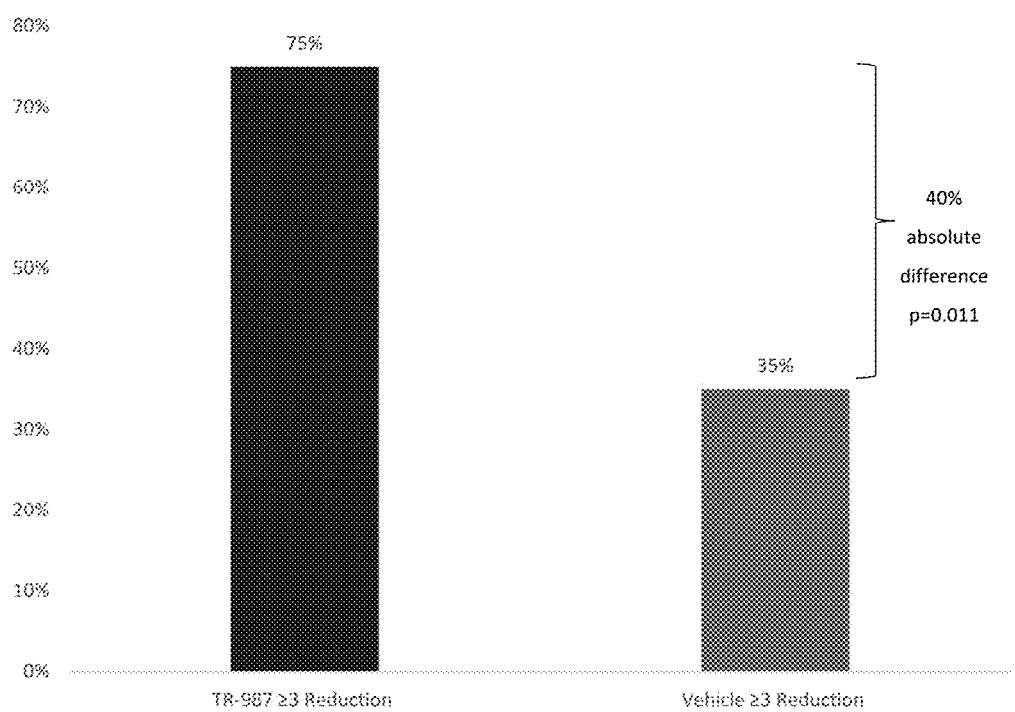
FIG. 19 illustrates the proportion of patients within each of the invention compound and vehicle groups who achieved a ≥3-point improvement in elastosis scores at day 28 (Fitzpatrick-Goldman Classification). A chi square test for unadjusted proportions was used to determine significance expressed as a p value. 75% of responders achieved an improvement score of 3 or greater in elastosis for the active group versus only 35% of responders for the placebo group at 28 days (a 114% variance P<0.011)

FIG. 19 details the proportion of patients within each of the invention compound and vehicle groups who achieved a ≥3-point improvement in elastosis scores between baseline and day 28 (Fitzpatrick-Goldman Classification). A chi square test for unadjusted proportions was used to determine significance expressed as a p value.

Example 17

In this example, the efficacy of the invention compound is tested against a further art product marketed as Woulgan™ and published as U.S. Pat. No. 9,956,245 B2 which was considered by the inventors to be the most relevant β-glucan patent publication for wound healing.

Figure 20:
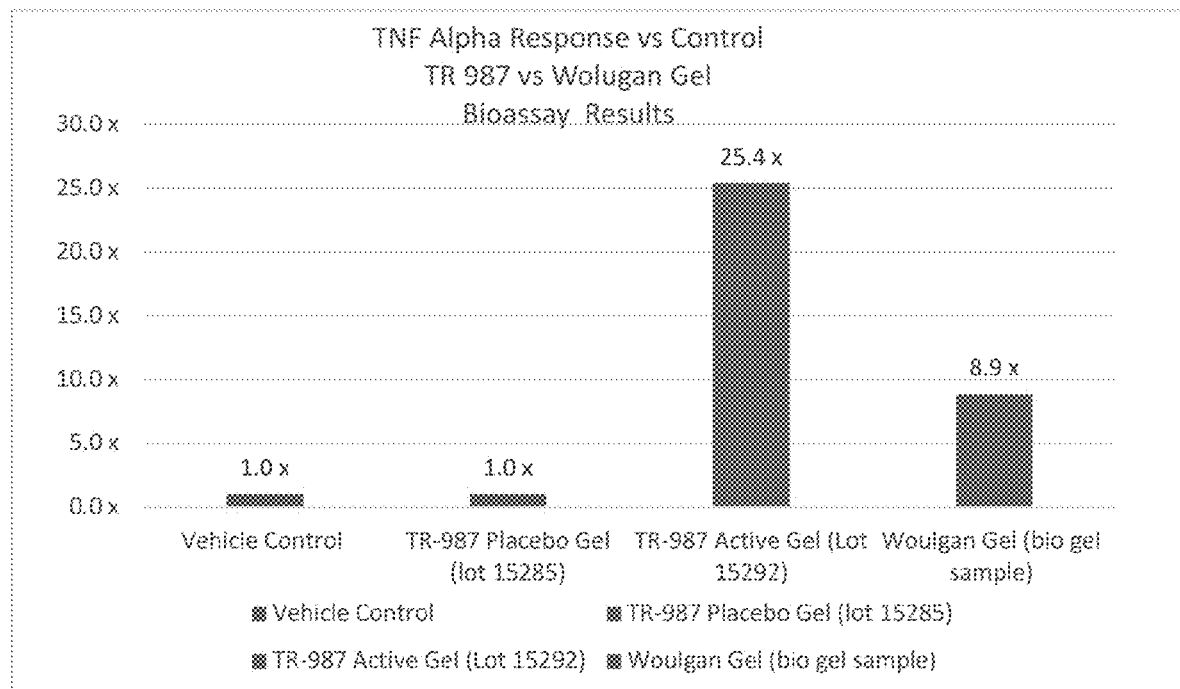
FIG. 20 illustrates, the efficacy of the invention compound against a further art product termed Woulgan™ which was considered by the inventors to be the most relevant β-glucan patent publication for wound healing. Woulgan™ produced an 8.9× immune response vs a control as measured by an assay measuring TNF alpha response from human harvested macrophage cells. By contrast, the invention compound assayed a 25.4× response for the invention compound (labelled TR-987) vs the same vehicle control. This implies that the invention compound is approximately 3× more potent than Woulgan™ gel, a very high increase in efficacy than an art compound.

As shown in FIG. 20, Woulgan™ produced an 8.9× immune response vs a control as measured by an assay measuring TNF Alpha response from human harvested macrophage cells. This is a measure of the immune response or stimulation. By contrast, the invention compound labelled TR-987 assayed a 25.4× response for the invention compound vs the same vehicle control. This implies that the invention compound is approximately 3× more potent than Woulgan™ gel, a very high increase in efficacy than an art compound. It is noted the concentration of Woulgan™ was 2%, the concentration of the invention compound (0.1%), Invention compound was present at $\frac{1}{20}^{th}$ the concentration of Woulgan™ gel but produced 3× the immune response, implying a molecule that is 60× as potent in generating an immune response Aspects of the polysaccharide compound, methods of use and methods of manufacture thereof have been described by way of example only and it should be appreciated that modifications and additions may be made thereto without departing from the scope of the claims herein.

What is claimed is:

1. A method of manufacturing an isolated biological polysaccharide compound, the isolated biological polysaccharide compound comprising:
   glycosyl linkages comprising 1:3 linked glucopyranosyl residue of 65-95% wt and 1:6 linked glucopyranosyl residue of 5-25% wt;
   a purity of 85-100% β-D-glucan;
   a molecular weight of 0.5 to 2.2 MDa; and,
   a TNF-alpha cytokine response in a human bioassay that is at least 1.5 times greater than a negative control TNF-alpha cytokine response in a human bioassay;
   wherein said isolated biological polysaccharide compound is essentially insoluble in aqueous solutions;
the method comprising:
   selecting yeast cells;
   lysing the yeast cells and collecting cell wall fragments;
   acidifying then heating the cell wall fragments to remove mannan and additional chitin;

conducting phase separation with a solvent to remove additional mannan and chitin along with proteins, glycogen and lipids;

separating solvent and other non-polysaccharide compounds via boiling and drying; and, performing at least one water rinse step after lysing and before acidifying.

2. The method as claimed in claim 1 where in the method further comprises at least one water rinse after said acidifying and before said phase separation.

3. The method as claimed in claim 1 further comprising, after acidifying and prior to said phase separation, changing pH and alcohol washing.

4. The method as claimed in claim 3 wherein the pH is reduced to 4.0 and said alcohol is washed, then increased to pH 9.0 and said alcohol is washed, then adjusted to pH 7.0 and said alcohol is washed.

5. The method as claimed in claim 1 wherein the method further comprises, post separation of the solvent and the other non-polysaccharide compounds via boiling and drying, further purifying through at least one additional series of solvent rinses, alcohol rinses and optionally, further water rinses before a final product is again dried.

6. The method as claimed in claim 1 wherein the yeast cells selected are from species *Saccharomyces cerevisiae*.

7. The method as claimed in claim 1 wherein lysing occurs via alkali treatment or heat treatment or both treatments.

8. The method as claimed in claim 3 wherein the alcohol used is selected from one or more lower alcohols.

9. The method as claimed in claim 3 wherein the alcohol used is selected from methanol, ethanol, propanol, and combinations thereof.

10. The method as claimed in claim 1 wherein the solvent used is: an organic solvent; and a non-polar solvent; and has a specific gravity greater than 1.0.

11. The method as claimed in claim 1 wherein the solvent is selected from: methyl chloroform, chloroform, dichloromethane, tetrachloroethane, carbon tetrachloride, ethyl acetate, and combinations thereof.

12. The method as claimed in claim 1 wherein the phase separation with said solvent is completed at room temperature and neutral pH.

13. The method as claimed in claim 1 wherein, post separation of the solvent and said other non-polysaccharide compounds via boiling and drying, dried polysaccharide produced is further purified through at least one additional series of solvent rinses, alcohol rinses and optionally, at least one additional series of water rinses before a final product is again dried.

14. The method as claimed in claim 13 wherein the at least one additional series of said solvent rinses and said alcohol rinses are carried out using: solvents selected from: methyl chloroform, chloroform, dichloromethane, tetrachloroethane, carbon tetrachloride, ethyl acetate, and combinations thereof; and alcohols selected from: methanol, ethanol, propanol, and combinations thereof.

15. The method as claimed in claim 13 wherein the at least one additional series of said water rinses are completed using water at a temperature of greater than 50° C.

16. The method as claimed in claim 1 wherein the isolated biological polysaccharide compound produced by the method is further characterised by a compound comprising additional side chains selected from one or more of: 1:4 linked glucopyranosyl residue; 3:4 linked glucopyranosyl residue; 2:3 linked glucopyranosyl residue; 3:6 linked glucopyranosyl residue; 2:6 and 4:6 linked glucopyranosyl residue; 3:4:6 linked glucopyranosyl residue; and/or terminal linked glucopyranosyl residue.

17. The method as claimed in claim 1 wherein the isolated biological polysaccharide compound produced by the method is further characterised by a compound comprising additional side chains comprising: 1:4 linked glucopyranosyl residue 2-6%; 3:4 linked glucopyranosyl residue 0.01-0.5%; 2:3 linked glucopyranosyl residue 0.5-4%; 3:6 linked glucopyranosyl residue 3-10%; 2:6 and 4:6 linked glucopyranosyl residue 0.2-1%; 3:4:6 linked glucopyranosyl residue 0.01-0.5%; and terminal linked glucopyranosyl residue 2-8%.

* * * * *